(12) United States Patent
Bouma et al.

(10) Patent No.: US 8,965,487 B2
(45) Date of Patent: Feb. 24, 2015

(54) PROCESS, SYSTEM AND SOFTWARE ARRANGEMENT FOR MEASURING A MECHANICAL STRAIN AND ELASTIC PROPERTIES OF A SAMPLE

(75) Inventors: Brett Eugene Bouma, Quincy, MA (US); Raymond C. Chan, Brookline, MA (US); Guillermo J. Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 2823 days.

(21) Appl. No.: 11/211,482

(22) Filed: Aug. 24, 2005

(65) Prior Publication Data

US 2006/0058592 A1    Mar. 16, 2006

Related U.S. Application Data

(60) Provisional application No. 60/604,137, filed on Aug. 24, 2004.

(51) Int. Cl.
*A61B 5/02* (2006.01)
*A61B 5/00* (2006.01)

(52) U.S. Cl.
CPC .............. *A61B 5/0066* (2013.01); *A61B 5/0059* (2013.01); *A61B 5/02007* (2013.01)
USPC ........................................................ 600/476

(58) Field of Classification Search
USPC ......... 600/476, 473, 479, 480, 477, 475, 309, 600/310, 407; 250/599.39, 208.1, 363.02, 250/363.04, 216, 559.4; 356/245, 346, 347, 356/345; 73/861.52; 362/553
See application file for complete search history.

(56) References Cited

U.S. PATENT DOCUMENTS 2,339,754 A    1/1944    Brace
3,090,753 A    5/1963    Matuszak et al.
(Continued)

FOREIGN PATENT DOCUMENTS

CN    1550203    12/2004
DE    4105221    9/1991
(Continued)

OTHER PUBLICATIONS

Marc Nikles et al., "Brillouin gain spectrum characterization in single-mode optical fibers", *Journal of Lightwave Technology* 1997, 15 (10): 1842-1851.
(Continued)

*Primary Examiner* — Long V Le
*Assistant Examiner* — Lawrence Laryea
(74) *Attorney, Agent, or Firm* — Andrews Kurth LLP

(57) ABSTRACT

A system, process and software arrangement are provided to determining data associated with at least one structural change of tissue. In particular, a first optical coherence tomography ("OCT") signal which contains first information regarding the tissue at a first stress level, and a second OCT signal which contains second information regarding the tissue at a second stress level are received. The first and second information are compared to produce comparison information. The data associated with the at least one structural change is determined as a function of the comparison information and further information associated with (i) at least one known characteristics of the tissue and/or (ii) characteristics of an OCT system. Further, at least one optical coherence tomography ("OCT") signal which contains information regarding the tissue can be received, and the modulus of the tissue may be determined as a function of the received at least one OCT signal.

58 Claims, 7 Drawing Sheets

(56) References Cited

U.S. PATENT DOCUMENTS

| | | | |
|---|---|---|---|
| 3,601,480 A | | 8/1971 | Randall |
| 3,856,000 A | | 12/1974 | Chikama |
| 3,872,407 A | | 3/1975 | Hughes |
| 3,901,074 A | * | 8/1975 | Douglas .................. 73/657 |
| 3,941,121 A | | 3/1976 | Olinger |
| 3,973,219 A | | 8/1976 | Tang et al. |
| 3,983,507 A | | 9/1976 | Tang et al. |
| 4,030,827 A | | 6/1977 | Delhaye et al. |
| 4,030,831 A | | 6/1977 | Gowrinathan |
| 4,140,364 A | | 2/1979 | Yamashita et al. |
| 4,141,362 A | | 2/1979 | Wurster |
| 4,224,929 A | | 9/1980 | Furihata |
| 4,295,738 A | | 10/1981 | Meltz et al. |
| 4,300,816 A | | 11/1981 | Snitzer et al. |
| 4,303,300 A | | 12/1981 | Pressiat et al. |
| 4,428,643 A | | 1/1984 | Kay |
| 4,479,499 A | | 10/1984 | Alfano |
| 4,533,247 A | | 8/1985 | Epworth |
| 4,585,349 A | | 4/1986 | Gross et al. |
| 4,601,036 A | | 7/1986 | Faxvog et al. |
| 4,607,622 A | | 8/1986 | Fritch et al. |
| 4,631,498 A | | 12/1986 | Cutler |
| 4,639,999 A | | 2/1987 | Daniele |
| 4,650,327 A | | 3/1987 | Ogi |
| 4,734,578 A | | 3/1988 | Horikawa |
| 4,744,656 A | | 5/1988 | Moran et al. |
| 4,751,706 A | | 6/1988 | Rohde et al. |
| 4,763,977 A | | 8/1988 | Kawasaki et al. |
| 4,770,492 A | | 9/1988 | Levin et al. |
| 4,827,907 A | | 5/1989 | Tashiro et al. |
| 4,834,111 A | | 5/1989 | Khanna et al. |
| 4,868,834 A | | 9/1989 | Fox et al. |
| 4,890,901 A | | 1/1990 | Cross, Jr. |
| 4,892,406 A | | 1/1990 | Waters |
| 4,905,169 A | | 2/1990 | Buican et al. |
| 4,909,631 A | | 3/1990 | Tan et al. |
| 4,925,302 A | | 5/1990 | Cutler |
| 4,928,005 A | | 5/1990 | Lefèvre et al. |
| 4,940,328 A | | 7/1990 | Hartman |
| 4,965,441 A | | 10/1990 | Picard |
| 4,965,599 A | | 10/1990 | Roddy et al. |
| 4,966,589 A | | 10/1990 | Kaufman |
| 4,984,888 A | | 1/1991 | Tobias et al. |
| 4,993,834 A | | 2/1991 | Carlhoff et al. |
| 4,998,972 A | | 3/1991 | Chin et al. |
| 5,039,193 A | | 8/1991 | Snow et al. |
| 5,040,889 A | | 8/1991 | Keane |
| 5,045,936 A | | 9/1991 | Lobb et al. |
| 5,046,501 A | | 9/1991 | Crilly |
| 5,065,331 A | | 11/1991 | Vachon et al. |
| 5,085,496 A | | 2/1992 | Yoshida et al. |
| 5,120,953 A | | 6/1992 | Harris |
| 5,121,983 A | | 6/1992 | Lee |
| 5,127,730 A | | 7/1992 | Brelje et al. |
| 5,148,807 A | * | 9/1992 | Hsu .................. 600/402 |
| 5,197,470 A | | 3/1993 | Helfer et al. |
| 5,202,745 A | | 4/1993 | Sorin et al. |
| 5,202,931 A | | 4/1993 | Bacus et al. |
| 5,208,651 A | | 5/1993 | Buican |
| 5,212,667 A | | 5/1993 | Tomlinson et al. |
| 5,214,538 A | | 5/1993 | Lobb |
| 5,217,456 A | | 6/1993 | Narciso, Jr. |
| 5,228,001 A | | 7/1993 | Birge et al. |
| 5,241,364 A | | 8/1993 | Kimura et al. |
| 5,248,876 A | | 9/1993 | Kerstens et al. |
| 5,250,186 A | | 10/1993 | Dollinger et al. |
| 5,251,009 A | | 10/1993 | Bruno |
| 5,262,644 A | | 11/1993 | Maguire |
| 5,275,594 A | | 1/1994 | Baker |
| 5,281,811 A | | 1/1994 | Lewis |
| 5,283,795 A | | 2/1994 | Fink |
| 5,291,885 A | | 3/1994 | Taniji et al. |
| 5,293,872 A | | 3/1994 | Alfano et al. |
| 5,293,873 A | | 3/1994 | Fang |
| 5,302,025 A | | 4/1994 | Kleinerman |
| 5,304,173 A | | 4/1994 | Kittrell et al. |
| 5,304,810 A | | 4/1994 | Amos |
| 5,305,759 A | | 4/1994 | Kaneko et al. |
| 5,317,389 A | | 5/1994 | Hochberg et al. |
| 5,318,024 A | | 6/1994 | Kittrell et al. |
| 5,321,501 A | | 6/1994 | Swanson et al. |
| 5,333,144 A | | 7/1994 | Liedenbaum et al. |
| 5,348,003 A | | 9/1994 | Caro |
| 5,353,790 A | | 10/1994 | Jacques et al. |
| 5,383,467 A | | 1/1995 | Auer et al. |
| 5,394,235 A | | 2/1995 | Takeuchi et al. |
| 5,404,415 A | | 4/1995 | Mori et al. |
| 5,411,016 A | | 5/1995 | Kume et al. |
| 5,419,323 A | | 5/1995 | Kittrell et al. |
| 5,424,827 A | | 6/1995 | Horwitz et al. |
| 5,439,000 A | | 8/1995 | Gunderson et al. |
| 5,441,053 A | | 8/1995 | Lodder et al. |
| 5,450,203 A | | 9/1995 | Penkethman |
| 5,454,807 A | | 10/1995 | Lennox et al. |
| 5,459,325 A | | 10/1995 | Hueton et al. |
| 5,459,570 A | | 10/1995 | Swanson et al. |
| 5,465,147 A | | 11/1995 | Swanson |
| 5,486,701 A | | 1/1996 | Norton et al. |
| 5,491,524 A | | 2/1996 | Hellmuth et al. |
| 5,491,552 A | | 2/1996 | Kittrell |
| 5,495,771 A | * | 3/1996 | Sumi et al. .................. 73/789 |
| 5,522,004 A | | 5/1996 | Djupsjobacka et al. |
| 5,526,338 A | | 6/1996 | Hasman et al. |
| 5,555,087 A | | 9/1996 | Miyagawa et al. |
| 5,562,100 A | | 10/1996 | Kittrell et al. |
| 5,565,983 A | | 10/1996 | Barnard et al. |
| 5,565,986 A | | 10/1996 | Knüttel |
| 5,566,267 A | | 10/1996 | Neuberger |
| 5,583,342 A | | 12/1996 | Ichie |
| 5,590,660 A | | 1/1997 | MacAulay et al. |
| 5,600,486 A | | 2/1997 | Gal et al. |
| 5,601,087 A | | 2/1997 | Gunderson et al. |
| 5,621,830 A | | 4/1997 | Lucey et al. |
| 5,623,336 A | | 4/1997 | Raab et al. |
| 5,635,830 A | | 6/1997 | Itoh |
| 5,649,924 A | | 7/1997 | Everett et al. |
| 5,696,579 A | * | 12/1997 | Johnson .................. 356/35.5 |
| 5,697,373 A | | 12/1997 | Richards-Kortum et al. |
| 5,698,397 A | | 12/1997 | Zarling et al. |
| 5,710,630 A | | 1/1998 | Essenpreis et al. |
| 5,716,324 A | | 2/1998 | Toida |
| 5,719,399 A | | 2/1998 | Alfano et al. |
| 5,730,731 A | | 3/1998 | Mollenauer et al. |
| 5,735,276 A | | 4/1998 | Lemelson |
| 5,740,808 A | | 4/1998 | Panescu et al. |
| 5,748,318 A | | 5/1998 | Maris et al. |
| 5,748,598 A | | 5/1998 | Swanson et al. |
| 5,752,518 A | | 5/1998 | McGee et al. |
| 5,784,352 A | | 7/1998 | Swanson et al. |
| 5,785,651 A | | 7/1998 | Kuhn et al. |
| 5,795,295 A | | 8/1998 | Hellmuth et al. |
| 5,801,826 A | | 9/1998 | Williams |
| 5,801,831 A | | 9/1998 | Sargoytchev et al. |
| 5,803,082 A | | 9/1998 | Stapleton et al. |
| 5,807,261 A | | 9/1998 | Benaron et al. |
| 5,810,719 A | | 9/1998 | Toida |
| 5,817,144 A | | 10/1998 | Gregory |
| 5,836,877 A | | 11/1998 | Zavislan et al. |
| 5,840,023 A | | 11/1998 | Oraevsky et al. |
| 5,840,031 A | | 11/1998 | Crowley |
| 5,840,075 A | | 11/1998 | Mueller et al. |
| 5,842,995 A | | 12/1998 | Mahadevan-Jansen et al. |
| 5,843,000 A | | 12/1998 | Nishioka et al. |
| 5,843,052 A | | 12/1998 | Benja-Athon |
| 5,847,827 A | | 12/1998 | Fercher |
| 5,862,273 A | | 1/1999 | Pelletier |
| 5,865,754 A | | 2/1999 | Sevick-Muraca et al. |
| 5,867,268 A | | 2/1999 | Gelikonov et al. |
| 5,871,449 A | | 2/1999 | Brown |
| 5,872,879 A | | 2/1999 | Hamm |
| 5,877,856 A | | 3/1999 | Fercher |
| 5,887,009 A | | 3/1999 | Mandella et al. |
| 5,892,583 A | | 4/1999 | Li |
| 5,910,839 A | | 6/1999 | Erskine et al. |

(56) References Cited

U.S. PATENT DOCUMENTS

| | | | |
|---|---|---|---|
| 5,912,764 A | 6/1999 | Togino | |
| 5,920,373 A | 7/1999 | Bille | |
| 5,920,390 A * | 7/1999 | Farahi et al. | 356/477 |
| 5,921,926 A | 7/1999 | Rolland et al. | |
| 5,926,592 A | 7/1999 | Harris et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |
| 5,968,064 A | 10/1999 | Selmon et al. | |
| 5,975,697 A | 11/1999 | Podoleanu et al. | |
| 5,983,125 A | 11/1999 | Alfano et al. | |
| 5,987,346 A | 11/1999 | Benaron et al. | |
| 5,991,697 A | 11/1999 | Nelson et al. | |
| 5,994,690 A * | 11/1999 | Kulkarni et al. | 250/216 |
| 5,995,223 A | 11/1999 | Power | |
| 6,002,480 A | 12/1999 | Izatt et al. | |
| 6,004,314 A | 12/1999 | Wei et al. | |
| 6,006,128 A * | 12/1999 | Izatt et al. | 600/476 |
| 6,007,996 A | 12/1999 | McNamara et al. | |
| 6,010,449 A | 1/2000 | Selmon et al. | |
| 6,014,214 A | 1/2000 | Li | |
| 6,016,197 A | 1/2000 | Krivoshlykov | |
| 6,020,963 A | 2/2000 | Dimarzio et al. | |
| 6,025,956 A | 2/2000 | Nagano et al. | |
| 6,033,721 A | 3/2000 | Nassuphis | |
| 6,037,579 A | 3/2000 | Chan et al. | |
| 6,044,288 A | 3/2000 | Wake et al. | |
| 6,045,511 A | 4/2000 | Ott et al. | |
| 6,048,742 A | 4/2000 | Weyburne et al. | |
| 6,053,613 A | 4/2000 | Wei et al. | |
| 6,069,698 A * | 5/2000 | Ozawa et al. | 356/511 |
| 6,078,047 A | 6/2000 | Mittleman et al. | |
| 6,091,496 A | 7/2000 | Hill | |
| 6,091,984 A | 7/2000 | Perelman et al. | |
| 6,094,274 A | 7/2000 | Yokoi | |
| 6,107,048 A | 8/2000 | Goldenring et al. | |
| 6,111,645 A | 8/2000 | Tearney et al. | |
| 6,117,128 A | 9/2000 | Gregory | |
| 6,120,516 A | 9/2000 | Selmon et al. | |
| 6,134,003 A | 10/2000 | Tearney et al. | |
| 6,134,010 A | 10/2000 | Zavislan | |
| 6,134,033 A | 10/2000 | Bergano et al. | |
| 6,141,577 A | 10/2000 | Rolland et al. | |
| 6,151,522 A | 11/2000 | Alfano et al. | |
| 6,159,445 A | 12/2000 | Klaveness et al. | |
| 6,160,826 A | 12/2000 | Swanson et al. | |
| 6,161,031 A | 12/2000 | Hochman et al. | |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,245,026 B1 | 6/2001 | Campbell et al. | |
| 6,249,349 B1 | 6/2001 | Lauer | |
| 6,249,381 B1 | 6/2001 | Suganuma | |
| 6,249,630 B1 | 6/2001 | Stock et al. | |
| 6,263,234 B1 | 7/2001 | Engelhardt et al. | |
| 6,264,610 B1 | 7/2001 | Zhu | |
| 6,272,268 B1 | 8/2001 | Miller et al. | |
| 6,272,376 B1 | 8/2001 | Marcu et al. | |
| 6,274,871 B1 | 8/2001 | Dukor et al. | |
| 6,276,798 B1 * | 8/2001 | Gil et al. | 351/206 |
| 6,282,011 B1 | 8/2001 | Tearney et al. | |
| 6,297,018 B1 | 10/2001 | French et al. | |
| 6,301,048 B1 | 10/2001 | Cao et al. | |
| 6,308,092 B1 | 10/2001 | Hoyns | |
| 6,324,419 B1 | 11/2001 | Guzelsu et al. | |
| 6,341,036 B1 | 1/2002 | Tearney et al. | |
| 6,353,693 B1 | 3/2002 | Kano et al. | |
| 6,359,692 B1 | 3/2002 | Groot | |
| 6,374,128 B1 | 4/2002 | Toida et al. | |
| 6,377,349 B1 | 4/2002 | Fercher | |
| 6,381,015 B1 * | 4/2002 | Sonehara et al. | 356/497 |
| 6,384,915 B1 | 5/2002 | Everett et al. | |
| 6,393,312 B1 | 5/2002 | Hoyns | |
| 6,394,964 B1 | 5/2002 | Sievert, Jr. et al. | |
| 6,396,941 B1 | 5/2002 | Bacus et al. | |
| 6,421,164 B2 | 7/2002 | Tearney et al. | |
| 6,437,867 B2 | 8/2002 | Zeylikovich et al. | |
| 6,441,892 B2 | 8/2002 | Xiao et al. | |
| 6,441,959 B1 | 8/2002 | Yang et al. | |
| 6,445,485 B1 | 9/2002 | Frigo et al. | |
| 6,445,939 B1 | 9/2002 | Swanson et al. | |
| 6,445,944 B1 | 9/2002 | Ostrovsky | |
| 6,459,487 B1 | 10/2002 | Chen et al. | |
| 6,463,313 B1 | 10/2002 | Winston et al. | |
| 6,469,846 B2 | 10/2002 | Ebizuka et al. | |
| 6,475,159 B1 | 11/2002 | Casscells et al. | |
| 6,475,210 B1 | 11/2002 | Phelps et al. | |
| 6,477,403 B1 | 11/2002 | Eguchi et al. | |
| 6,485,413 B1 | 11/2002 | Boppart et al. | |
| 6,485,482 B1 | 11/2002 | Belef | |
| 6,494,834 B2 * | 12/2002 | Konofagou et al. | 600/438 |
| 6,501,551 B1 | 12/2002 | Tearney et al. | |
| 6,501,878 B2 | 12/2002 | Hughes et al. | |
| 6,516,014 B1 | 2/2003 | Sellin et al. | |
| 6,517,532 B1 | 2/2003 | Altshuler et al. | |
| 6,538,817 B1 | 3/2003 | Farmer et al. | |
| 6,540,391 B2 * | 4/2003 | Lanzetta et al. | 362/553 |
| 6,549,801 B1 | 4/2003 | Chen et al. | |
| 6,552,796 B2 | 4/2003 | Magnin et al. | |
| 6,556,305 B1 | 4/2003 | Aziz et al. | |
| 6,556,853 B1 | 4/2003 | Cabib et al. | |
| 6,558,324 B1 | 5/2003 | Von Behren et al. | |
| 6,560,259 B1 | 5/2003 | Hwang | |
| 6,564,087 B1 | 5/2003 | Pitris et al. | |
| 6,564,089 B2 | 5/2003 | Izatt et al. | |
| 6,567,585 B2 | 5/2003 | Harris | |
| 6,581,011 B1 * | 6/2003 | Johnson et al. | 702/19 |
| 6,593,101 B2 | 7/2003 | Richards-Kortum et al. | |
| 6,611,833 B1 | 8/2003 | Johnson et al. | |
| 6,615,071 B1 | 9/2003 | Casscells, III et al. | |
| 6,622,732 B2 | 9/2003 | Constantz | |
| 6,654,127 B2 | 11/2003 | Everett et al. | |
| 6,657,730 B2 | 12/2003 | Pfau et al. | |
| 6,658,278 B2 | 12/2003 | Gruhl | |
| 6,680,780 B1 | 1/2004 | Fee | |
| 6,685,885 B2 | 2/2004 | Nolte et al. | |
| 6,687,007 B1 | 2/2004 | Meigs | |
| 6,687,010 B1 | 2/2004 | Horii et al. | |
| 6,687,036 B2 | 2/2004 | Riza | |
| 6,692,430 B2 | 2/2004 | Adler | |
| 6,701,181 B2 | 3/2004 | Tang et al. | |
| 6,721,094 B1 | 4/2004 | Sinclair et al. | |
| 6,725,073 B1 | 4/2004 | Motamedi et al. | |
| 6,738,144 B1 | 5/2004 | Dogariu et al. | |
| 6,741,355 B2 | 5/2004 | Drabarek | |
| 6,757,467 B1 | 6/2004 | Rogers | |
| 6,790,175 B1 | 9/2004 | Furusawa et al. | |
| 6,806,963 B1 | 10/2004 | Wälti et al. | |
| 6,816,743 B2 | 11/2004 | Moreno et al. | |
| 6,831,781 B2 | 12/2004 | Tearney et al. | |
| 6,839,496 B1 | 1/2005 | Mills et al. | |
| 6,882,432 B2 | 4/2005 | Deck | |
| 6,900,899 B2 | 5/2005 | Nevis | |
| 6,903,820 B2 | 6/2005 | Wang | |
| 6,909,105 B1 | 6/2005 | Heintzmann et al. | |
| 6,949,072 B2 | 9/2005 | Furnish et al. | |
| 6,961,123 B1 | 11/2005 | Wang et al. | |
| 6,980,299 B1 | 12/2005 | de Boer | |
| 6,996,549 B2 | 2/2006 | Zhang et al. | |
| 7,006,231 B2 | 2/2006 | Ostrovsky et al. | |
| 7,006,232 B2 | 2/2006 | Rollins et al. | |
| 7,019,838 B2 | 3/2006 | Izatt et al. | |
| 7,027,633 B2 | 4/2006 | Foran et al. | |
| 7,048,691 B2 * | 5/2006 | Miele et al. | 600/504 |
| 7,061,622 B2 | 6/2006 | Rollins et al. | |
| 7,072,047 B2 | 7/2006 | Westphal et al. | |

(56) References Cited

U.S. PATENT DOCUMENTS

| | | |
|---|---|---|
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 * | 6/2007 | Tearney et al. ............... 600/407 |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,474,407 B2 * | 1/2009 | Gutin ............................ 356/479 |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0095087 A1 * | 7/2002 | Mourad et al. ............... 600/442 |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0078486 A1 * | 4/2003 | Klein et al. .................... 600/398 |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0187342 A1 * | 10/2003 | Cuzzani et al. ............... 600/399 |
| 2003/0199769 A1 | 10/2003 | Podoleanu et al. |
| 2003/0208190 A1 * | 11/2003 | Roberts et al. .................... 606/5 |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0034304 A1 * | 2/2004 | Sumi ............................ 600/439 |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0234113 A1 * | 11/2004 | Miga ............................ 382/128 |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0254474 A1 | 12/2004 | Seibel et al. |
| 2004/0258116 A1 | 12/2004 | Araujo et al. |
| 2004/0258762 A1 * | 12/2004 | Boppart et al. ............... 424/491 |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 * | 8/2005 | Chen et al. .................... 600/476 |
| 2005/0190372 A1 * | 9/2005 | Dogariu ....................... 356/479 |
| 2005/0197530 A1 | 9/2005 | Wallace et al. |
| 2005/0221270 A1 | 10/2005 | Connelly et al. |
| 2005/0254061 A1 | 11/2005 | Alphonse et al. |
| 2005/0271590 A1 * | 12/2005 | Schwartz et al. ............. 424/9.5 |
| 2006/0020172 A1 | 1/2006 | Luerssen et al. |
| 2006/0033923 A1 | 2/2006 | Hirasawa et al. |

(56) References Cited

U.S. PATENT DOCUMENTS

| | | |
|---|---|---|
| 2006/0039004 A1 | 2/2006 | de Boer et al. |
| 2006/0052696 A1* | 3/2006 | Shiina et al. ............... 600/437 |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Osypka et al. |
| 2006/0171503 A1 | 8/2006 | O'Hara et al. |
| 2006/0184048 A1 | 8/2006 | Saadat et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0021275 A1 | 1/2008 | Tearney et al. |
| 2008/0049220 A1 | 2/2008 | Izzia et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0204762 A1 | 8/2008 | Izatt et al. |
| 2008/0228086 A1 | 9/2008 | Ilegbusi |
| 2008/0234560 A1 | 9/2008 | Nomoto et al. |
| 2008/0265130 A1 | 10/2008 | Colomb et al. |
| 2008/0308730 A1 | 12/2008 | Vizi et al. |
| 2009/0005691 A1 | 1/2009 | Huang |
| 2009/0011948 A1 | 1/2009 | Uniu et al. |
| 2009/0051923 A1 | 2/2009 | Zuluaga |
| 2009/0131801 A1 | 5/2009 | Suter et al. |
| 2009/0192358 A1 | 7/2009 | Jaffer et al. |
| 2009/0196477 A1 | 8/2009 | Cense et al. |
| 2009/0273777 A1 | 11/2009 | Yun et al. |
| 2009/0281390 A1 | 11/2009 | Qiu et al. |
| 2009/0290156 A1 | 11/2009 | Popescu et al. |
| 2009/0305309 A1 | 12/2009 | Chien et al. |
| 2010/0002241 A1 | 1/2010 | Hirose |
| 2010/0086251 A1 | 4/2010 | Xu et al. |
| 2010/0094576 A1 | 4/2010 | de Boer et al. |
| 2010/0150467 A1 | 6/2010 | Zhao et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 62-188001 | 6/1989 |
| JP | 04-056907 | 2/1992 |
| JP | 20040056907 | 2/1992 |
| JP | 4135550 | 5/1992 |
| JP | 4135551 | 5/1992 |
| JP | 5509417 | 11/1993 |
| JP | 9-230248 | 9/1997 |
| JP | 10-267631 | 10/1998 |
| JP | 2000-046729 | 2/2000 |
| JP | 2000-121961 | 4/2000 |
| JP | 2000-504234 | 4/2000 |
| JP | 2001-174404 | 6/2001 |
| JP | 2001-174744 | 6/2001 |
| JP | 2001-508340 | 6/2001 |
| JP | 2007-539336 | 6/2001 |
| JP | 2001-212086 | 8/2001 |
| JP | 2001525580 | 12/2001 |
| JP | 2002-205434 | 2/2002 |
| JP | 2002-095663 | 4/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2005-062850 | 3/2005 |
| JP | 2005-110208 | 4/2005 |
| JP | 2005-195485 | 7/2005 |
| JP | 2007271761 | 10/2007 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9848846 | 11/1998 |
| WO | 9905487 | 2/1999 |
| WO | 9944089 | 2/1999 |
| WO | 9944089 | 9/1999 |
| WO | 99-45338 | 10/1999 |
| WO | 9957507 | 11/1999 |
| WO | 00-42906 | 7/2000 |
| WO | 0058766 | 10/2000 |
| WO | 0101111 | 1/2001 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0237075 | 5/2002 |
| WO | 0238040 | 5/2002 |
| WO | 02053050 | 7/2002 |
| WO | 02054027 | 7/2002 |
| WO | 02-083003 | 10/2002 |
| WO | 02084263 | 10/2002 |
| WO | 03-012405 | 2/2003 |
| WO | 03020119 | 3/2003 |
| WO | 03046495 | 6/2003 |
| WO | 03046636 | 6/2003 |

(56) References Cited

FOREIGN PATENT DOCUMENTS

| WO | 03052478 | 6/2003 |
|---|---|---|
| WO | 03062802 | 7/2003 |
| WO | 03-088826 | 10/2003 |
| WO | 03105678 | 12/2003 |
| WO | 2004034869 | 4/2004 |
| WO | 2004-043251 | 5/2004 |
| WO | 2004057266 | 7/2004 |
| WO | 2004066824 | 8/2004 |
| WO | 2004088361 | 10/2004 |
| WO | 04105598 | 12/2004 |
| WO | 2005000115 | 1/2005 |
| WO | 2005047813 | 5/2005 |
| WO | 2005054780 | 6/2005 |
| WO | 2005082225 | 9/2005 |
| WO | 2006004743 | 1/2006 |
| WO | 2006014392 | 2/2006 |
| WO | 2006038876 | 4/2006 |
| WO | 2006039091 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007083138 | 7/2007 |
| WO | 2007084995 | 7/2007 |
| WO | 2009153929 | 12/2009 |
| WO | 2011-055376 | 5/2011 |

OTHER PUBLICATIONS

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23-S 27.

T. Yoshimura et al., "Statistical properties of dynamic speckles", *J. Opt. Soc. Am A.* 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2. 2002. pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastric Carcinoma in the United States." *American Cancer Society* vol. 83, No. 10 pp. 2049-2053.

Barr, H et al. (2005) "Endoscopic Therapy for Barrett's Oesophaugs" *Gut* vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastrorenterology* vol. 112, pp. 1787-1797.

(56) References Cited

OTHER PUBLICATIONS

Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 5, pp. 1321-1323

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4. pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetilcno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis" Precise Microsurgery by Selective Absorption of Pulsed Radiation *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Tang C. L. et al., "Wide-band electro-optical tuning of semiconductor lasers", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

(56) References Cited

OTHER PUBLICATIONS

Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19$^{th}$ International Conference—IEEE Oct. 30-Nov. 2, 1997. pp. 887-888.
Parker K. J. et al., "Techniques for Elastic Imaging: A Review", IEEE Engineering in Medicine and Biology, Nov./Dec. 1996, pp. 52-59.
European Patent Office Search Report for Application No. 05791226. 3.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
International Search Report for International Patent application No. PCT/US2005/043951.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664.
International Written Opinion for International Patent application No. PCT/US2005/023664.
Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704.
International Search Report for International Patent application No. PCT/US2004/039454.
International Written Opinion for International Patent application No. PCT/US2004/039454.
PCT International Preliminary Report on Patentability for International Application No. PCT/US2004/038404 dated Jun. 2, 2006.
Notice of Reasons for Rejection and English translation for Japanese Patent Application No. 2002-538830.
Fujimoto et al., "High Resolution in Vivo Intra-Arterial Imaging with Optical Coherence Tomography", Official Journal of the British Cardiac Society, vol. 82, pp. 128-133 Heart, 1999.
D. Huang et al., "Optical Coherence Tomography", Science, vol. 254, pp. 1178-1181, Nov. 1991.
Tearney et al., "High-Speed Phase- and Group Delay Scanning with a Grating Based Phase Control Delay Line", Optics Letters, vol. 22, pp. 1811-1813, Dec. 1997.
Rollins, et al., "In Vivo Video Rate Optical Coherence Tomography", Optics Express, vol. 3, pp. 219-229, Sep. 1998.
Saxer, et al., High Speed Fiber-Based Polarization-Sensitive Optical Coherence Tomography of in Vivo Human Skin, Optical Society of America, vol. 25, pp. 1355-1357, Sep. 2000.
Oscar Eduardo Martinez, "3000 Times Grating Compress or with Positive Group Velocity Dispersion", IEEE, vol. QE-23, pp. 59-64, Jan. 1987.
Kulkarni, et al., "Image Enhancement in Optical Coherence Tomography Using Deconvolution", Electronics Letters, vol. 33, pp. 1365-1367, Jul. 1997.
Bashkansky, et al., "Signal Processing for Improving Field Cross-Correlation Function in Optical Coherence Tomography", Optics & Photonics News, vol. 9, pp. 8137-8138, May 1998.
Yung et al., "Phase-Domain Processing of Optical Coherence Tomography Images", Journal of Biomedical Optics, vol. 4, pp. 125-136, Jan. 1999.
Tearney, et al., "In Vivo Endoscopic Optical Biopsy with Optical Coherence Tomography", Science, vol. 276, Jun. 1997.
W. Drexler et al., "In Vivo Ultrahigh-Resolution Optical Coherence Tomography", Opt. Lett. vol. 24, pp. 1221-1223, Sep. 1999.
Nicusor V. Iftimia et al., "A Portable, Low Coherence Interferometry Based Instrument for Fine Needle Aspiration Biopsy Guidance" Accepted to Review of Scientific Instruments, 2005.
Abbas, G.L., V.W.S. Chan et al., "Local-Oscillator Excess-Noise Suppression for Homodyne and Heterodyne-Detection", Optics Letters, vol. 8, pp. 419-421, Aug. 1983 issue.
Agrawal, G.P., "Population Pulsations and Nondegenerate 4-Wave Mixing in Semiconductor-Lasers and Amplifiers", Journal of the Optical Society of America B-Optical Physics, vol. 5, pp. 147-159, Jan. 1998.
Andretzky, P. et al., "Optical Coherence Tomography by Spectral Radar: Improvement of Signal-to-Noise Ratio", The International Society for Optical Engineering, USA, vol. 3915, 2000.
Ballif, J. et al., "Rapid and Scalable Scans at 21 m/s in optical Low-Coherence Reflectometry", Optics Letters, vol. 22, pp. 757-759, Jun. 1997.
Barfuss H. et al., "Modified Optical Frequency-Domain Reflectometry with High Spatial-Resolution for Components of Integrated Optic Systems", Journal of Lightwave Technology, vol. 7, pp. 3-10, Jan. 1989.
Beaud, P. et al., "Optical Reflectometry with Micrometer Resolution for the Investigation of Integrated Optical-Devices", Ieee Journal of Quantum Electronics, vol. 25, pp. 755-759, Apr. 1989.
Bouma, Brett et al., "Power-Efficient Nonreciprocal Interferometer and Linear-Scanning Fiber-Optic Catheter for Optical Coherence Tomography", Optics Letters, vol. 24, pp. 531-533, Apr. 1999.
Brinkmeyer, E. et al., "Efficient Algorithm for Non-Equidistant Interpolation of Sampled Data", Electronics Letters, vol. 28, p. 693, Mar. 1992.
Brinkmeyer, E. et al., "High-Resolution OCDR in Dispersive Wave-Guides", Electronics Letters, vol. 26, pp. 413-414, Mar. 1990.

(56) References Cited

OTHER PUBLICATIONS

Chinn, S.R. et al., "Optical Coherence Tomography Using a Frequency-Tunable Optical Source", *Optics Letters*, vol. 22, pp. 340-342, Mar. 1997.
Danielson, B.L. et al., "Absolute Optical Ranging Using Low Coherence Interferometry", *Applied Optics*, vol. 30, p. 2975, Jul. 1991.
Dorrer, C. et al., "Spectral Resolution and Sampling Issues in Fourier-Transform Spectral Interferometry", *Journal of the Optical Society of America B—Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments", *Optics Express*, vol. 10, p. 1215, Oct. 2002.
Eickhoff, W. et al., "Optical Frequency-Domain Reflectometry in Single-Mode Fiber", *Applied Physics Letters*, vol. 39, pp. 693-695, 1981.
Fercher, Adolf "Optical Coherence Tomography", *Journal of Biomedical Optics*, vol. 1, pp. 157-173, Apr. 1996
Ferreira, L.A. et al., "Polarization-Insensitive Fiberoptic White-Light Interferometry", *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver", *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides", *Journal of Lightwave Technology*, vol. 11, pp. 1377-1384, Aug. 1993
Golubovic, B. et al., "Optical Frequency-Domain Reflectometry Using Rapid Wavelength Tuning of a Cr4+:Forsterite Laser", *Optics Letters*, vol. 11, pp. 1704-1706, Nov. 1997.
Haberland, U. H. P. et al., "Chirp Optical Coherence Tomography of Layered Scattering Media", *Journal of Biomedical Optics*, vol. 3, pp. 259-266, Jul. 1998.
Hammer, Daniel X. et al., "Spectrally Resolved White-Light Interferometry for Measurement of Ocular Dispersion", *Journal of the Optical Society of America A—Optics Image Science and Vision*, vol. 16, pp. 2092-2102, Sep. 1999.
Harvey, K. C. et al., "External-Cavity Diode-Laser Using a Grazing-Incidence Diffraction Grating", *Optics Letters*, vol. 16, pp. 910-912, Jun. 1991.
Hausler, Gerd et al., "'Coherence Radar' and 'Spectral Radar' New Tools for Dermatological Diagnosis", *Journal of Biomedical Optics*, vol. 3, pp. 21-31, Jan. 1998.
Hee, Michael R. et al., "Polarization-Sensitive Low-Coherence Reflectometer for Birefringence Characterization and Ranging", *Journal of the Optical Society of America B (Optical Physics)*, vol. 9, p. 903-908, Jun. 1992.
Hotate Kazuo et al., "Optical Coherence Domain Reflectometry by Synthesis of Coherence Function", *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier", *Applied Physics Letters*, vol. 51, pp. 1051-1053, 1987.
Ivanov, A. P. et al., "New Method for High-Range Resolution Measurements of Light Scattering in Optically Dense Inhomogeneous Media", *Optics Letters*, vol. 1, pp. 226-228, Dec. 1977.
Ivanov, A. P. et al., "Interferometric Study of the Spatial Structure of a Light-Scattering Medium", *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths", *Applied Optics*, vol. 22, pp. 706-710, Mar. 1983.
Kersey, A. D. et al., "Adaptive Polarization Diversity Receiver Configuration for Coherent Optical Fiber Communications", *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm", *Journal of Lightwave Technology*, vol. 9, pp. 1493-1502, Nov. 1991.
Larkin, Kieran G., "Efficient Nonlinear Algorithm for Envelope Detection in White Light Interferometry", *Journal of the Optical Society of America A—Optics Image Science and Vision*, vol. 13, pp. 832-843, Apr. 1996.
Leitgeb, R. et al., "Spectral measurement of Absorption by Spectroscopic Frequency-Domain Optical Coherence Tomography", *Optics Letters*, vol. 25, pp. 820-822, Jun. 2000.
Lexer, F. et al., "Wavelength-Tuning Interferometry of Intraocular Distances", *Applied Optics*, vol. 36, pp. 6548-6553, Sep. 1997.
Mitsui, Takahisa, "Dynamic Range of Optical Reflectometry with Spectral Interferometry", *Japanese Journal of Applied Physics Part 1—Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light", *Optics Letters*, vol. 15, pp. 393-395, Apr. 1990.
Okoshi, Takanori, "Polarization-State Control Schemes for Heterodyne or Homodyne Optical Fiber Communications", *Journal of Lightwave Technology*, vol. LT-3, pp. 1232-1237, Dec. 1995.
Passy, R. et al., "Experimental and Theoretical Investigations of Coherent OFDR with Semiconductor-Laser Sources", *Journal of Lightwave Technology*, vol. 12, pp. 1622-1630, Sep. 1994.
Podoleanu, Adrian G., "Unbalanced Versus Balanced Operation in an Optical Coherence Tomography System", *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier", *Journal of the Optical Society of America B—Optical Physics*, vol. 19, pp. 1286-1294, Jun. 2002.
Schmitt, J. M. et al, "Measurement of Optical-Properties O Biological Tissues by Low-Coherence Reflectometry" *Applied Optics*, vol. 32, pp. 6032-6042, Oct. 1993.
Silberberg, Y. et al., "Passive-Mode Locking of a Semiconductor Diode-Laser", *Optics Letters*, vol. 9, pp. 507-509, Nov. 1984.
Smith, L. Montgomery et al., "Absolute Displacement Measurements Using Modulation of the Spectrum of White-Light in a Michelson Interferometer", *Applied Optics*, vol. 28, pp. 3339-3342, Aug. 1989.
Sonnenschein, C. M. et al., "Signal-To-Noise Relationships for Coaxial Systems that Heterodyne Backscatter from Atmosphere", *Applied Optics*, vol. 10, pp. 1600-1604, Jul. 1971.
Sorin, W. V. et al., "Measurement of Rayleigh Backscattering at 1.55 mu m with 32 mu m Spatial Resolution", *IEEE Photonics Technology Letters*, vol. 4, pp. 374-376, Apr. 1992.
Sorin, W. V. et al., "A Simple Intensity Noise-Reduction Technique for Optical Low-Coherence Reflectometry", *IEEE Photonics Technology Letters*, vol. 4, pp. 1404-1406, Dec. 1992.
Swanson, E. A. et al., "High-Speed Optical Coherence Domair Reflectometry", *Optics Letters*, vol. 17, pp. 151-153, Jan. 1992.
Takada, K. et al., "High-Resolution OFDR with Incorporated Fiberoptic Frequency Encoder", *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry", *IEEE Photonics Technology Letters*, vol. 8, pp. 658-660, May 1996.
Takada, Kazumasa et al., "New Measurement System for Fault Location in Optical Wave-Guide Devices Based on an Interometric-Technique", *Applied Optics*, vol. 26, pp. 1603-1606, May 1987.
Tateda, Mitsuhiro et al., "Interferometric Method for Chromatic Dispersion Measurement in a Single-Mode Optical Fiber", *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method", *Applied Physics B (Photophysics and Laser Chemistry)*, vol. B52, pp. 391-394, 1991.
Trutna, W. R. et al., "Continuously Tuned External-Cavity Semiconductor-Laser", *Journal of Lightwave Technology*, vol. 11, pp. 1279-1286, Aug. 1993.

(56) References Cited

OTHER PUBLICATIONS

Uttam, Deepak et al., "Precision Time Domain Reflectometry in Optical Fiber Systems Using a Frequency Modulated Continuous Wave Ranging Technique", Journal of *Lightwave Technology*, vol. 3, pp. 971-977, Oct. 1985.
Von Der Weid, J. P. et al., "On the Characterization of Optical Fiber Network Components with Optical Frequency Domain Reflectometry", Journal of *Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M", *Optics Letters*, vol. 15, pp. 879-881, Aug. 1990.
Youngquist, Robert C. et al., "Optical Coherence-Domain Reflectometry—A New Optical Evaluation Technique", *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic Tunable Filter", *IEEE Journal of Selected Topics in Quantum Electronics*, vol. 3, pp. 1087-1096, Aug. 1997.
Yun, S. H. et al., "Interrogation of Fiber Grating Sensor Arrays with a Wavelength-Swept Fiber Laser", *Optics Letters*, vol. 23, pp. 843-845, Jun. 1998.
Yung, K. M., "Phase-Domain Processing of Optical Coherence Tomography Images", *Journal of Biomedical Optics*, vol. 4, pp. 125-136, Jan. 1999.
Zhou, Xiao-Qun et al., "Extended-Range FMCW Reflectometry Using an optical Loop with a Frequency Shifter", *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers", *Journal of Lightwave Technology*, vol. 13, pp. 62-66, Jan. 1995.
Victor S. Y. Lin et al., "A Porous Silicon-Based Optical Interferometric Biosensor", *Science Magazine*, vol. 278, pp. 840-843, Oct. 31, 1997.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.
Roth, Jonathan E. et al., "Simplified Method for Polarization-Sensitive Optical Coherence Tomography," *Optics Letters*, vol. 26, No. 14, Jul. 15, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wang, Xueding et al., "Propagation of Polarized Light in Birefringent Turbid Media: Time-Resolved Simulations," Optical Imaging Laboratory, Biomedical Engineering Program, Texas A&M University.
Wong, Brian J.F. et al., "Optical Coherence Tomography of the Rat Cochlea," Journal of *Biomedical Optics*, vol. 5, No. 4, Oct. 2000, pp. 367-370.

(56) References Cited

OTHER PUBLICATIONS

Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Bréhonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.
De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.
Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.
Schmitt, J.M. et al., "Cross-Polarized Backscatter in Optical Coherence Tomography of Biological Tissue," *Optics Letters*, vol. 23, No. 13, Jul. 1, 1998, pp. 1060-1062.
Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.
Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurement of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stiffer, D. et al., "Polarisation-Sensitive Optical Coherence Tomography for Material Characterisation and Strain-Field Mapping," *Applied Physics A 76, Materials Science & Processing*, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.

(56) References Cited

OTHER PUBLICATIONS

Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin In Vivo," 2004, *Optical Society of America*.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., "Comment on Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc.* 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.
Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.

(56) References Cited

OTHER PUBLICATIONS

H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 µm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics" 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report mailed Dec. 14, 2010 for EP 10182301.1.
S. Hell et al., "Breaking the diffraction resolution limit by stimulated-emission—stimulated-emission depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nonometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluoresence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
Lee et al., "The Unstable Artheroma," Arteriosclerosis, Thrombosis & Vascular Biology, 17:1859-67 (1997).
International Search report dated Sep. 13, 2010 for PCT/US2010/023215.
International Search Report dated Feb. 23, 2011 for PCT/US2010/041923.
International Search Report dated Apr. 29, 2011 for PCT/US2010/051715.
Feng et al., "Mesocopic Conductors and corrections in Lasers Speckle Patters" Science, New Series, vol. 251, No. 4994, pp. 633-639 (Feb. 8, 1991).
A.A. Bednov et al., "Investigation of Statistical Properties of Lymph Flow Dynamics Using Speckle-Microscopy," SPIE, 2981:181-90 (1997).
V. Tuchin et al., Speckle Interferometer in the measurements of Biotissues Vibrations SPIE, 1647:125 (1992).
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.

(56) References Cited

OTHER PUBLICATIONS

Japanese Notice of Grounds for Rejection dated Dec. 28, 2011 for JP2008-535793.
Japanese Notice of Reasons for Rejection dated Dec. 12, 2011 for JP 2008-533712.
International Search Report and Written Opinion mailed Feb. 9, 2012 based on PCT/US2011/034810.
International Search Report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.
Acioli, L. H., M. Ulman, et al. (1991). "Femtosecond Temporal Encoding in Barium-Titanate." *Optics Letters* 16(24): 1984-1986.
Aigouy, L., A. Lahrech, et al. (1999). "Polarization effects in apertureless scanning near-field optical microscopy: an experimental study." *Optics Letters* 24(4): 187-189.
Akiba, M., K. P. Chan, et al. (2003). "Full-field optical coherence tomography by two-dimensional heterodyne detection with a pair of CCD cameras." *Optics Letters* 28(10): 816-818.
Akkin, T., D. P. Dave, et al. (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensitivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.
Antcliff, R. J., T. J. ffytche, et al. (2000). "Optical coherence tomography of melanocytoma." *American Journal of Ophthalmology* 130(6): 845-7.
Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.
Anvari, B., T. E. Milner, et al. (1995). "Selective Cooling of Biological Tissues—Application for Thermally Mediated Therapeutic Procedures." *Physics in Medicine and Biology* 40(2): 241-252.
Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.
Arend, O., M. Ruffer, et al. (2000). "Macular circulation in patients with diabetes mellitus with and without arterial hypertension." *British Journal of Ophthalmology* 84(12): 1392-1396.
Arimoto, H. and Y. Ohtsuka (1997). "Measurements of the complex degree of spectral coherence by use of a wave-front-folded interferometer." *Optics Letters* 22(13): 958-960.
Azzolini, C., F. Patelli, et al. (2001). "Correlation between optical coherence tomography data and biomicroscopic interpretation of idiopathic macular hole." *American Journal of Ophthalmology* 132(3): 348-55.
Baba, T., K. Ohno-Matsui, et al. (2002). "Optical coherence tomography of choroidal neovascularization in high myopia." *Acta Ophthalmoloqica Scandinavica* 80(1): 82-7.
Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.
Baney, D. M. and W. V. Sorin (1993). "Extended-Range Optical Low-Coherence Reflectometry Using a Recirculating Delay Technique." *Ieee Photonics Technology Letters* 5(9): 1109-1112.
Baney, D. M., B. Szafraniec, et al. (2002). "Coherent optical spectrum analyzer." *Ieee Photonics Technology Letters* 14(3): 355-357.
Barakat, R. (1981). "Bilinear Constraints between Elements of the 4by4 Mueller-Jones Transfer-Matrix of Polarization Theory." *Optics Communications* 38(3): 159-161.
Barakat, R. (1993). "Analytic Proofs of the Arago-Fresnel Laws for the Interference of Polarized-Light." *Journal of the Optical Society of America a—Optics Image Science and Vision* 10(1): 180-185.
Barbastathis, G. and D. J. Brady (1999). "Multidimensional tomographic imaging using volume holography." *Proceedings of the Ieee* 87(12): 2098-2120.
Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.
Barsky, S. H., S. Rosen, et al. (1980). "Nature and Evolution of Port Wine Stains—Computer-Assisted Study." *Journal of Investigative Dermatology* 74(3): 154-157.
Barton, J. K., J. A. Izatt, et al. (1999). "Three-dimensional reconstruction of blood vessels from in vivo color Doppler optical coherence tomography images." *Dermatology* 198(4): 355-361.
Barton, J. K., A. Rollins, et al. (2001). "Photothermal coagulation of blood vessels: a comparison of high-speed optical coherence tomography and numerical modelling." *Physics in Medicine and Biology* 46.
Barton, J. K., A. J. Welch, et al. (1998). "Investigating pulsed dye laser-blood vessel interaction with color Doppler optical coherence tomography." *Optics Express* 3.
Bashkansky, M., M. D. Duncan, et al. (1997). "Subsurface defect detection in ceramics by high-speed high-resolution optical coherent tomography." *Optics Letters* 22 (1): 61-63.
Bashkansky, M. and J. Reintjes (2000). "Statistics and reduction of speckle in optical coherence tomography." *Optics Letters* 25(8): 545-547.
Baumgartner, A., S. Dichtl, et al. (2000). "Polarization-sensitive optical coherence tomography of dental structures." *Caries Research* 34(1): 59-69.
Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.
Baumgartner, A., C. K. Hitzenberger, et al. (1998). "Signal and resolution enhancements in dual beam optical coherence tomography of the human eye." *Journal of Biomedical Optics* 3(1): 45-54.
Beaurepaire, E., P. Gleyzes, et at. (1998). *Optical coherence microscopy for the in-depth study of biological structures: System based on parallel detection scheme*, Proceedings of SPIE—The International Society for Optical Engineering.
Beaurepaire, E., L. Moreaux, et al. (1999). "Combined scanning optical coherence and two-photon-excited fluorescence microscopy." *Optics Letters* 24(14): 969-971.
Bechara, F. G., T. Gambichler, et al. (2004). "Histomorphologic correlation with routine histology and optical coherence tomography." *Skin Research and Technology* 10 (3): 169-173.
Bechmann, M., M. J. Thiel, et al. (2000). "Central corneal thickness determined with optical coherence tomography in various types of glaucoma. [see comments]." *British Journal of Ophthalmology* 84(11): 1233-7.
Bek, T. and M. Kandi (2000). "Quantitative anomaloscopy and optical coherence tomography scanning in central serous chorioretinopathy." *Acta Ophthalmologica Scandinavica* 78(6): 632-7.
Benoit, A. M., K. Naoun, et al. (2001). "Linear dichroism of the retinal nerve fiber layer expressed with Mueller matrices." *Applied Optics* 40(4): 565-569.
Bicout, D., C. Brosseau, et al. (1994). "Depolarization of Multiply Scattered Waves by Spherical Diffusers—Influence of the Size Parameter." *Physical Review* E 49(2): 1767-1770.

(56) References Cited

OTHER PUBLICATIONS

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3.

Bouma, B. E., M. Ramaswamy-Paye, et al. (1997). "Compact resonator designs for mode-locked solid-state lasers." *Applied Physics B (Lasers and Optics)* B65.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a—Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

(56) References Cited

OTHER PUBLICATIONS

Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama—Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.
Dave, D. P. and T. E. Milner (2000). "Doppler-angle measurement in highly scattering media." *Optics Letters* 25(20): 1523-1525.
de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.
de Boer, J. F., C. E. Saxer, et al. (2001). "Stable carrier generation and phase-resolved digital data processing in optical coherence tomography." *Applied Optics* 40(31): 5787-5790.
Degroot, P. and L. Deck (1993). "3-Dimensional Imaging by Sub-Nyquist Sampling of White-Light Interferograms." *Optics Letters* 18(17): 1462-1464.
Denk, W., J. H. Strickler, et al. (1990). "2-Photon Laser Scanning Fluorescence Microscopy." *Science* 248(4951): 73-76.
Descour, M. R., A. H. O. Karkkainen, et al. (2002). "Toward the development of miniaturized Imaging systems for detection of precancer." *Ieee Journal of Quantum Electronics* 38(2): 122-130.
Dettwiller, L. (1997). "Polarization state interference: A general investigation." *Pure and Applied Optics* 6(1): 41-53.
DiCarlo, C. D., W. P. Roach, et al. (1999). "Comparison of optical coherence tomography imaging of cataracts with histopathology." *Journal of Biomedical Optics* 4.
Ding, Z., Y. Zhao, et al. (2002). "Real-time phase-resolved optical coherence tomography and optical Doppler tomography." *Optics Express* 10(5): 236-245.
Dobrin, P. B. (1996). "Effect of histologic preparation on the cross-sectional area of arterial rings." *Journal of Surgical Research* 61(2): 413-5.
Donohue, D. J., B. J. Stoyanov, et al. (1995). "Numerical Modeling of the Corneas Lamellar Structure and Birefringence Properties." *Journal of the Optical Society of America a—Optics Image Science and Vision* 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.
Drexler, W., A. Baumgartner, et al. (1997). "Biometric investigation of changes in the anterior eye segment during accommodation." *Vision Research* 37(19): 2789-2800.
Drexler, W., A. Baumgartner, et al. (1997). "Submicrometer precision biometry of the anterior segment of the human eye." *Investigative Ophthalmology & Visual Science* 38(7): 1304-1313.
Drexler, W., A. Baumgartner, et al. (1998). "Dual beam optical coherence tomography: signal identification for ophthalmologic diagnosis." *Journal of Biomedical Optics* 3 (1): 55-65.
Drexler, W., O. Findl, et al. (1998). "Partial coherence interferometry: A novel approach to biometry in cataract surgery." *American Journal of Ophthalmology* 126(4): 524-534.
Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.
Drexler, W., C. K. Hitzenberger, et al. (1995). "Measurement of the Thickness of Fundus Layers by Partial Coherence Tomography." *Optical Engineering* 34(3): 701-710.
Drexler, W., U. Morgner, et al. (2001). "Ultrahigh-resolution ophthalmic optical coherence tomography." *Nature Medicine* 7(4): 502-507.
Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.
Drexler, W., H. Sattmann, et al. (2003). "Enhanced visualization of macular pathology with the use of ultrahigh-resolution optical coherence tomography." *Archives of Ophthalmology* 121(5): 695-706.
Drexler, W., D. Stamper, et al. (2001). "Correlation of collagen organization with polarization sensitive imaging of in vitro cartilage: implications for osteoarthritis." *Journal of Rheumatology* 28(6): 1311-8.
Droog, E. J., W. Steenbergen, et al. (2001). "Measurement of depth of burns by laser Doppler perfusion imaging." *Burns* 27(6): 561-8.
Dubois, A., K. Grieve, et al. (2004). "Ultrahigh-resolution full-field optical coherence tomography." *Applied Optics* 43(14): 2874-2883.
Dubois, A., L. Vabre, et al. (2002). "High-resolution full-field optical coherence tomography with a Linnik microscope." *Applied Optics* 41(4): 805-812.
Ducros, M., M. Laubscher, et al. (2002). "Parallel optical coherence tomography in scattering samples using a two-dimensional smart-pixel detector array." *Optics Communications* 202(1-3): 29-35.
Ducros, M. G., J. D. Marsack, et al. (2001). "Primate retina imaging with polarization-sensitive optical coherence tomography." *Journal of the Optical Society of America a—Optics Image Science and Vision* 18(12): 2945-2956.
Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.
Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.
Eisenbeiss, W., J. Marotz, et al. (1999). "Reflection-optical multispectral imaging method for objective determination of burn depth." *Burns* 25(8): 697-704.
Elbaum, M., M. King, et al. (1972). "Wavelength-Diversity Technique for Reduction of Speckle Size." *Journal of the Optical Society of America* 62(5): 732-&.
Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

(56) References Cited

OTHER PUBLICATIONS

Essenpreis, M., C. E. Elwell, et al. (1993). "Spectral Dependence of Temporal Point Spread Functions in Human Tissues." *Applied Optics* 32(4): 418-425.
Eun, H. C. (1995). "Evaluation of skin blood flow by laser Doppler flowmetry. [Review] [151 refs]." *Clinics in Dermatology* 13(4): 337-47.
Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.
Feldchtein, F. I., G. V. Gelikonov, et al. (1998). "In vivo OCT imaging of hard and soft tissue of the oral cavity." *Optics Express* 3(6): 239-250.
Feldchtein, F. I., G. V. Gelikonov, et al. (1998). "Endoscopic applications of optical coherence tomography." *Optics Express* 3(6): 257-270.
Fercher, A. F., W. Drexler, et al. (1997). "Optical ocular tomography." *Neuro-Ophthalmology* 18(2): 39-49.
Fercher, A. F., W. Drexler, et al. (1994). *Measurement of optical distances by optical spectrum modulation.* Proceedings of SPIE—The International Society for Optical Engineering.
Fercher, A. F., W. Drexler, et al. (2003). "Optical coherence tomography—principles and applications." *Reports on Progress in Physics* 66(2): 239-303.
Fercher, A. F., C. Hitzenberger, et al. (1991). "Measurement of Intraocular Optical Distances Using Partially Coherent Laser-Light." *Journal of Modern Optics* 38(7): 1327-1333.
Fercher, A. F., C. K. Hitzenberger, et al. (1996). *Ocular partial coherence interferometry*, Proceedings of SPIE—The International Society for Optical Engineering.
Fercher, A. F., C. K. Hitzenberger, et al. (1993). "In-Vivo Optical Coherence Tomography." *American Journal of Ophthalmology* 116(1): 113-115.
Fercher, A. F., C. K. Hitzenberger, et al. (1994). *In-vivo dual-beam optical coherence tomography.* Proceedings of SPIE—The International Society for Optical Engineering.
Fercher, A. F., C. K. Hitzenberger, et al. (1995). "Measurement of Intraocular Distances by Backscattering Spectral Interferometry." *Optics Communications* 117(1-2): 43-48.
Fercher, A. F., C. K. Hitzenberger, et al. (2000). "A thermal light source technique for optical coherence tomography." *Optics Communications* 185(1-3): 57-64.
Fercher, A. F., C. K. Hitzenberger, et al. (2001). "Numerical dispersion compensation for Partial Coherence Interferometry and Optical Coherence Tomography." *Optics Express* 9(12): 610-615.
Fercher, A. F., C. K. Hitzenberger, et al. (2002). "Dispersion compensation for optical coherence tomography depth-scan signals by a numerical technique." *Optics Communications* 204(1-6): 67-74.
Fercher, A. F., H. C. Li, et al. (1993). "Slit Lamp Laser-Doppler Interferometer." *Lasers in Surgery and Medicine* 13(4): 447-452.
Fercher, A. F., K. Mengedoht, et at. (1988). "Eye-Length Measurement by Interferometry with Partially Coherent-Light." *Optics Letters* 13(3): 186-188.
Ferro, P., M. Haelterman, et al. (1991). "All-Optical Polarization Switch with Long Low-Birefringence Fiber." *Electronics Letters* 27(16): 1407-1408.
Fetterman, M. R., D. Goswami, et al. (1998). "Ultrafast pulse shaping: amplification and characterization." *Optics Express* 3(10): 366-375.
Findl, O., W. Drexler, et al. (2001). "Improved prediction of intraocular lens power using partial coherence interferometry." *Journal of Cataract and Refractive Surgery* 27 (6): 861-867.
Fork, R. L., C. H. B. Cruz, et al. (1987). "Compression of Optical Pulses to 6 Femtoseconds by Using Cubic Phase Compensation." *Optics Letters* 12(7): 483-485.
Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto, J. G., M. E. Brezinski, et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Optical Engineering* 20(1): 25-30.
Galtarossa, A., L. Palmieri, et al. (2000). "Statistical characterization of fiber random birefringence." *Optics Letters* 25(18): 1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikonov, V. M., G. V. Gelikonov, et al. (1995). "Coherent Optical Tomography of Microscopic Inhomogeneities in Biological Tissues." *Jetp Letters* 61(2): 158-162.
George, N. and A. Jain (1973). "Speckle Reduction Using Multiple Tones of Illumination." *Applied Optics* 12(6): 1202-1212.
Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a—Optics Image Science and Vision* 17(2): 328-334.
Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologic correlation of pig retina radial stratification with ultrahigh-resolution optical coherence tomography." *Investigative Ophthalmoloqy & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.
Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

(56) References Cited

OTHER PUBLICATIONS

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics*.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmoloqv* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in volume scatterers with 10(11)-fold slow motion." *Optics Letters* 21(14): 1087-1089.
Hazebroek, H. F. and A. A. Holscher (1973). "Interferometric Ellipsometry." *Journal of Physics E—Scientific Instruments* 6(9): 822-826.
Hazebroek, H. F. and W. M. Visser (1983). "Automated Laser Interferometric Ellipsometry and Precision Reflectometry." *Journal of Physics E—Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Topography of diabetic macular edema with optical coherence tomography." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Welle (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vivo, ultrahigh-resolution optical coherence tomography." *Optics Letters* 29(19): 2261-2263.
Hirakawa, H., H. Iijima, et al. (1999). "Optical coherence tomography of cystoid macular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.
Hitzenberger, C. K., A. Baumgartner, et al. (1999). "Dispersion effects in partial coherence interferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154 (4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., A. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Hotate, K. and T. Okugawa (1994). "Optical Information-Processing by Synthesis of the Coherence Function." *Journal of Lightwave Technology* 12(7): 1247-1255.
Hourdakis, C. J. and A. Perris (1995). "A Monte-Carlo Estimation of Tissue Optical-Properties for Use in Laser Dosimetry." *Physics in Medicine and Biology* 40(3): 351-364.
Hu, Z., F. Li, et al. (2000). "Wavelength-tunable narrow-linewidth semiconductor fiber-ring laser." *IEEE Photonics Technology Letters* 12(8): 977-979.

(56) References Cited

OTHER PUBLICATIONS

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a—Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmoloqy* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomoghraghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a—Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

(56) References Cited

OTHER PUBLICATIONS

Kesen, M. R., G. L. Spaeth, et al. (2002). "The Heidelberg Retina Tomograph vs clinical impression in the diagnosis of glaucoma." *American Journal of Ophthalmology* 133(5): 613-6.
Kienle, A. and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand, et al. (1994). "Differential Vascular-Response to Laser Photothermolysis." *Journal of Investigative Dermatology* 103(5): 693-700.
Kloppenberg, F. W. H., G. Beerthuizen, et al. (2001). "Perfusion of burn wounds assessed by Laser Doppler Imaging is related to burn depth and healing time." *Burns* 27(4): 359-363.
Knighton, R. W. and X. R. Huang (2002). "Analytical methods for scanning laser polarimetry." *Optics Express* 10(21): 1179-1189.
Knighton, R. W., X. R. Huang, et al. (2002). "Analytical model of scanning laser polarimetry for retinal nerve fiber layer assessment." *Investigative Ophthalmology & Visual Science* 43(2): 383-392.
Knuettel, A. R. S., Joseph M.; Shay, M.; Knutson, Jay R. (1994). "Stationary low-coherence light imaging and spectroscopy using a CCD camera." *Proc. SPIE*, vol. 2135: p. 239-250.
Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.
Knuttel, A. and J. M. Schmitt (1993). "Stationary Depth-Profiling Reflectometer Based on Low-Coherence Interferometry." *Optics Communications* 102(3-4): 193-198.
Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.
Kobayashi, M., H. Hanafusa, et al. (1991). "Polarization-Independent Interferometric Optical-Time-Domain Reflectometer." *Journal of Lightwave Technology* 9(5): 623-628.
Kolios, M. C., M. D. Sherar, et al. (1995). "Large Blood-Vessel Cooling in Heated Tissues—a Numerical Study." *Physics in Medicine and Biology* 40(4): 477-494.
Koozekanani, D., K. Boyer, et al. (2001). "Retinal thickness measurements from optical coherence tomography using a Markov boundary model." *Ieee Transactions on Medical Imaging* 20(9): 900-916.
Kop, R. H. J. and R. Sprik (1995). "Phase-sensitive interferometry with ultrashort optical pulses." *Review of Scientific Instruments* 66(12): 5459-5463.
Kramer, R. Z., J. Bella, et al. (1999). "Sequence dependent conformational variations of collagen triple-helical structure." *Nature Structural Biology* 6(5): 454-7.
Kulkarni, M. D., T. G. van Leeuwen, et al. (1998). "Velocity-estimation accuracy and frame-rate limitations in color Doppler optical coherence tomography." *Optics Letters* 23(13): 1057-1059.
Kwon, Y. H., C. S. Kim, et al. (2001). "Rate of visual field loss and long-term visual outcome in primary open-angle glaucoma." *American Journal of Ophthalmology* 132(1): 47-56.
Kwong, K. F., D. Yankelevich, et al. (1993). "400-Hz Mechanical Scanning Optical Delay-Line." *Optics Letters* 18(7): 558-560.
Landers, J., I. Goldberg, et al. (2002). "Analysis of risk factors that may be associated with progression from ocular hypertension to primary open angle glaucoma." *Clin Experiment Ophthalmogy* 30(4): 242-7.
Laszlo, A. and A. Venetianer (1998). Heat resistance in mammalian cells: Lessons and challenges. *Stress of Life.* 851: 169-178.
Laszlo, A. and A. Venetianer (1998). "Heat resistance in mammalian cells: lessons and challenges. [Review] [52 refs]." *Annals of the New York Academy of Sciences* 851: 169-78.
Laufer, J., R. Simpson, et al. (1998). "Effect of temperature on the optical properties of ex vivo human dermis and subdermis." *Physics in Medicine and Biology* 43(9): 2479-2489.
Lederer, D. E., J. S. Schuman, et al. (2003). "Analysis of macular volume in normal and glaucomatous eyes using optical coherence tomography." *American Journal of Ophthalmology* 135(6): 838-843.
Lee, P. P., Z. W. Feldman, et al. (2003). "Longitudinal prevalence of major eye diseases." *Archives of Ophthalmology* 121(9): 1303-1310.
Lehrer, M. S., T. T. Sun, et al. (1998). "Strategies of epithelial repair: modulation of stem cell and transit amplifying cell proliferation." *Journal of Cell Science* 111(Pt 19): 2867-75.
Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.
Leitgeb, R., C. K. Hitzenberger, et al. (2003). "Performance of fourier domain vs. time domain optical coherence tomography." *Optics Express* 11(8): 889-894.
Leitgeb, R., L. F. Schmetterer, et al. (2002). "Flow velocity measurements by frequency domain short coherence interferometry." *Proc. SPIE* 4619: 16-21.
Leitgeb, R. A., W. Drexler, et al. (2004). "Ultrahigh resolution Fourier domain optical coherence tomography." *Optics Express* 12(10): 2156-2165.
Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.
Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.
Leitgeb, R. A., L. Schmetterer, et al. (2004). "Real-time measurement of in vitro flow by Fourier-domain color Doppler optical coherence tomography." *Optics Letters* 29 (2): 171-173.
LeRoyBrehonnet, F. and B. LeJeune (1997). "Utilization of Mueller matrix formalism to obtain optical targets depolarization and polarization properties." *Progress in Quantum Electronics* 21(2): 109-151.
Leske, M. C., A. M. Connell, et al. (1995). "Risk factors for open-angle glaucoma. The Barbados Eye Study. [see comments]." *Archives of Ophthalmology* 113(7): 918-24.
Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.
Leske, M. C., A. Heijl, et al. (1999). "Early Manifest Glaucoma Trial. Design and Baseline Data." *Ophthalmology* 106(11): 2144-2153.
Lewis, S. E., J. R. DeBoer, et al. (2005). "Sensitive, selective, and analytical improvements to a porous silicon gas sensor." *Sensors and Actuators B: Chemical* 110(1): 54-65.
Lexer, F., C. K. Hitzenberger, et al. (1999). "Dynamic coherent focus OCT with depth-independent transversal resolution." *Journal of Modern Optics* 46(3): 541-553.
Li, X., C. Chudoba, et al. (2000). "Imaging needle for optical coherence tomography." *Optics Letters* 25: 1520-1522.
Li, X., T. H. Ko, et al. (2001). "Intraluminal fiber-optic Doppler imaging catheter for structural and functional optical coherence tomography." *Optics Letters* 26: 1906-1908.
Liddington, M. I. and P. G. Shakespeare (1996). "Timing of the thermographic assessment of burns." *Burns* 22(1): 26-8.
Lindmo, T., D. J. Smithies, et al. (1998). "Accuracy and noise in optical Doppler tomography studied by Monte Carlo simulation." *Physics in Medicine and Biology* 43(10): 3045-3064.
Liu, J., X. Chen, et al. (1999). "New thermal wave aspects on burn evaluation of skin subjected to instantaneous heating." *IEEE Transactions on Biomedical Engineering* 46(4): 420-8.
Luke, D. G., R. McBride, et al. (1995). "Polarization mode dispersion minimization in fiber-wound piezoelectric cylinders." *Optics Letters* 20(24): 2550-2552.

(56) References Cited

OTHER PUBLICATIONS

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.
Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.
Maitland, D. J. and J. T. Walsh, Jr. (1997). "Quantitative measurements of linear birefringence during heating of native collagen." *Lasers in Surgery & Medicine* 20 (3): 310-8.
Majaron, B., S. M. Srinivas, et al. (2000). "Deep coagulation of dermal collagen with repetitive Er:YAG laser irradiation." *Lasers in Surgery and Medicine* 26(2): 215-222.
Mansuripur, M. (1991). "Effects of High-Numerical-Aperture Focusing on the State of Polarization in Optical and Magnetooptic Data-Storage Systems." *Applied Optics* 30(22): 3154-3162.
Marshall, G. W., S. J. Marshall, et al. (1997). "The dentin substrate: structure and properties related to bonding." *Journal of Dentistry* 25(6): 441-458.
Martin, P. (1997). "Wound healing—Aiming for perfect skin regeneration." *Science* 276 (5309): 75-81.
Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.
Martinez, O. E., J. P. Gordon, et al. (1984). "Negative Group-Velocity Dispersion Using Refraction." *Journal of the Optical Society of America a—Optics Image Science and Vision* 1(10): 1003-1006.
McKinney, J. D., M. A. Webster, et al. (2000). "Characterization and imaging in optically scattering media by use of laser speckle and a variable-coherence source." *Optics Letters* 25(1): 4-6.
Miglior, S., M. Casula, et al. (2001). "Clinical ability of Heidelberg retinal tomograph examination to detect glaucomatous visual field changes." *Ophthalmology* 108 (9): 1621-7.
Milner, T. E., D. M. Goodman, et al. (1996). "Imaging laser heated subsurface chromophores in biological materials: Determination of lateral physical dimensions." *Physics in Medicine and Biology* 41(1): 31-44.
Milner, T. E., D. M. Goodman, et al. (1995). "Depth Profiling of Laser-Heated Chromophores in Biological Tissues by Pulsed Photothermal Radiometry." *Journal of the Optical Society of America a—Optics Image Science and Vision* 12 (7): 1479-1488.
Milner, T. E., D. J. Smithies, et al. (1996). "Depth determination of chromophores in human skin by pulsed photothermal radiometry." *Applied Optics* 35(19): 3379-3385.
Mishchenko, M. I. and J. W. Hovenier (1995). "Depolarization of Light Backscattered by Randomly Oriented Nonspherical Particles." *Optics Letters* 20(12): 1356-&.
Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.
Mitsui, T. (1999). "High-speed detection of ballistic photons propagating through suspensions using spectral interferometry." *Japanese Journal of Applied Physics Part 1—Regular Papers Short Notes & Review Papers* 38(5A): 2978-2982.
Molteno, A. C., N. J. Bosma, et al. (1999). "Otago glaucoma surgery outcome study: long-term results of trabeculectomy—1976 to 1995." *Ophthalmology* 106(9): 1742-50.
Morgner, U., W. Drexler, et al. (2000). "Spectroscopic optical coherence tomography." *Optics Letters* 25(2): 111-113.
Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.
Mourant, J. R., A. H. Hielscher, et al. (1998). "Evidence of intrinsic differences in the light scattering properties of tumorigenic and nontumorigenic cells." *Cancer Cytopathology* 84(6): 366-374.
Muller, M., J. Squier, et al. (1998). "Dispersion pre-compensation of 15 femtosecond optical pulses for high-numerical-aperture objectives." *Journal of Microscopy—Oxford* 191: 141-150.
Muscat, S., N. McKay, et al. (2002). "Repeatability and reproducibility of corneal thickness measurements by optical coherence tomography." *Investigative Ophthalmology & Visual Science* 43(6): 1791-5.
Musch, D. C., P. R. Lichter, et al. (1999). "The Collaborative Initial Glaucoma Treatment Study. Study Design, Methods, and Baseline Characteristics of Enrolled Patients." *Ophthalmology*_106: 653-662.
Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.
Nelson, J. S., K. M. Kelly, et al. (2001). "Imaging blood flow in human port-wine stain in situ and in real time using optical Doppler tomography." *Archives of Dermatology* 137(6): 741-744.
Newson, T. P., F. Farahi, et al. (1988). "Combined Interferometric and Polarimetric Fiber Optic Temperature Sensor with a Short Coherence Length Source." *Optics Communications* 68(3): 161-165.
November, L. J. (1993). "Recovery of the Matrix Operators in the Similarity and Congruency Transformations—Applications in Polarimetry." *Journal of the Optical Society of America a—Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678-680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multi-functional spectral-domain optical coherence tomography at 1.3 mu m." *Optics Express* 13(11): 3931-3944.
Park, D. H., J. W. Hwang, et al. (1998). "Use of laser Doppler flowmetry for estimation of the depth of burns." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.
Pircher, M., E. Gotzinger, et al. (2003). "Measurement and imaging of water concentration in human cornea with differential absorption optical coherence tomography." *Optics Express* 11(18): 2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and a confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.

(56) References Cited

OTHER PUBLICATIONS

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3x3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a—Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a—Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy."

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

(56) References Cited

OTHER PUBLICATIONS

Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis For imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.
Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003). "Differential spectral interferometry: an imaging technique for biomedical applications." *Optics Letters* 28(15): 1332-1334.
Vakoc, B. J., S. H. Yun, et al. (2005). "Phase-resolved optical frequency domain imaging." *Optics Express* 13(14): 5483-5493.
van Leeuwen, T. G., M. D. Kulkarni, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization." *Journal of the Optical Society of America a—Optics Image Science and Vision* 10(10): 2240-2245.
Vargas, O., E. K. Chan, et al. (1999). "Use of an agent to reduce scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by the use of optical Doppler tomography." *Applied Optics* 36(1): 144-149.
Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology—Head and Neck Surgery* 130(3): 334-338.
Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."
Yang, C., A. Wax, et al. (2001). "Phase-dispersion optical tomography." *Optics Letters* 26(10): 686-688.
Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." Optics Communications 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13) : 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Ophthalmoloqy* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23): 5614-5624.

(56) References Cited

OTHER PUBLICATIONS

Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.

Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19$^{th}$ Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers—Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.

(56) References Cited

OTHER PUBLICATIONS

International Search Report and Written Opinion dated Feb. 2, 2009 for International Application No. PCT/US2008/071786.
Bilenca A et al: "The Role of Amplitude andphase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.

\* cited by examiner

PROCESS, SYSTEM AND SOFTWARE ARRANGEMENT FOR MEASURING A MECHANICAL STRAIN AND ELASTIC PROPERTIES OF A SAMPLE

CROSS-REFERENCE TO RELATED APPLICATION(S)

The present invention claims priority from U.S. Patent Application Ser. No. 60/604,137 filed on Aug. 24, 2004, the entire disclosure of which incorporated herein by reference.

STATEMENT REGARDING FEDERALLY SPONSORED RESEARCH

This invention was made with government support under Grant No(s). DAMD17-99-2-9001 awarded by the U.S. Army Medical Research and Material Command. The government has certain rights in the invention.

FIELD OF THE INVENTION

The present invention relates generally measuring a mechanical strain and elastic properties of a sample, and more particularly, to a process, system and software arrangement for non-invasively measuring and determining a spatial distribution of a mechanical strain and elastic properties of biological samples.

BACKGROUND OF THE INVENTION

Myocardial infarction is a major cause of death in industrialized countries. Rupture of vulnerable atherosclerotic plaques has been recognized as an important mechanism for an acute myocardial infarction, which may often result in a sudden death. Recent advances in a cardiovascular research have identified structural and compositional features of atherosclerotic plaques that predispose them to rupture. In a majority of vulnerable plaques, these features include a) the presence of activated macrophages at the shoulder or edge of the plaque, b) a thin, unstable fibrous cap and c) a compliant lipid pool. The combination of biochemically initiated weakening, represented by these three features and elevated mechanical stress, may represent a particularly high-risk scenario.

A technique that is capable of detecting plaques vulnerable to rupture may become a valuable tool for guiding management of patients that are at risk, and can assist in the ultimate prevention of acute events. A number of different techniques have been under investigation for the detection of vulnerable plaques. These methods include intravascular ultrasound ("IVUS"), optical coherence tomography ("OCT"), fluorescence spectroscopy, magnetic resonance imaging ("MRI"), computed tomography ("CT"), positron-emission tomography ("PET") and infrared spectroscopy.

OCT is an imaging technique that can measure an interference between a reference beam of light and a detected beam reflected back from a sample. A detailed system description of conventional time-domain OCT has been provided in Huang et al. "Optical coherence tomography," Science 254 (5035), 1178-81 (1991). The spectral-domain variant of OCT, called spectral-domain optical coherence tomography ("SD-OCT"), is a technique that is suitable for ultrahigh-resolution ophthalmic imaging. This technique has been described in Cense, B. et al., "Ultrahigh-resolution high-speed retinal imaging using spectral-domain optical coherence tomography", Optics Express, 2004 and in International Patent Publication No. WO 03/062802. In addition, U.S. patent application Ser. No. 10/272,171 filed on Oct. 16, 2002, Wojtkowski et al., "In Vivo Human Retinal Imaging by Fourier Domain Optical Coherence Tomography", Journal of Biomedical Optics, 2002, 7(3), pp. 457-463, Nassif, N. et al., "In Vivo Human Retinal Imaging by Ultrahigh-Speed Spectral Domain Optical Coherence Tomography", Optics Letters, 2004, 29(5), pp. 480-482 also relates to this subject matter. In addition, optical frequency domain interferometry ("OFDI") setup (as described in Yun, S. H. et al., "High-Speed Optical Frequency-Domain Imaging", Optics Express, 2003, 11(22), pp. 2953-2963, International Publication No. WO 03/062802 and U.S. Patent Application Ser. No. 60/514,769 filed on Oct. 27, 2004 further relate to the subject matter of the present invention.

The SD-OCT and OFDI techniques are similar to the OCT technique in that they provide high-resolution, cross-sectional images of tissue. Such exemplary techniques also enable an accurate characterization of the tissue composition, and provide greatly improved image acquisition rates. These exemplary variants shall be collectively referred to herein as OCT. Of the above-described proposed techniques, OCT technique has been shown to be capable of spatially resolving structural and compositional features thought to be directly responsible for plaque rupture. However, the knowledge of structural and compositional features alone may be insufficient for a detailed understanding and accurate prediction of plaque rupture. A technique that combines structural/compositional information with the measurements of strain and elastic modulus would be preferable.

Certain numerical techniques (e.g., a finite element analysis) have been used for understanding the mechanical stress and strain, and their roles in plaque rupture. Various current analyses have relied upon models of vessel cross-sections based loosely on histology and IVUS, and have obtained either assumed or indirectly measured values for tissue elastic properties. Although these numerical techniques have provided some insight into the plaque rupture, they are disadvantageous because, e.g., a) their accuracy is limited by the imprecise knowledge of the elastic properties and their distribution; and b) they are based on retrospective data, and may not be directly applied to the assessment of the vascular structure in living patients.

IVUS elastography has been developed as a method for measuring the strain in vascular structures in vivo. This exemplary technique may be performed by acquiring multiple, cross-sectional images during a change in intravascular pressure. By correlating these images, the mechanical response of the vessel to the pressure change can be determined resulting in a cross-sectional map of strain, local displacement, deformation, or spatially resolved velocity. Although this technique can be performed in vivo, it provides a low spatial resolution and low contrast between typical tissue components in the atherosclerotic plaques. Further, such technique does not provide the ability to determine the stress independently from the strain, and therefore may not be capable of determining the elastic modulus distributions. OCT elastography technique is based on techniques related to those used in IVUS elastography. The OCT elastography technique can, in principle, provide higher resolution and relative elastic modulus distributions than IVUS elastography. When coupled with knowledge of the pressure load at the arterial lumen, high resolution estimates of absolute elastic moduli are also possible.

Doppler imaging techniques in conjunction with IVUS and OCT have been used for determining the depth-resolved velocity of samples toward or away from an imaging probe.

Although several variants of these technologies are known, a common basis is the measurement of the Doppler frequency shift imparted on a probe beam, ultrasound in IVUS and light in OCT, by moving scatterers within the sample.

However, the technique for simultaneously determining structure, composition and biomechanical properties of a sample is not available. This capability would have broad application in biomedicine, but in particular would be effective in detecting the vulnerable plaque and understanding its relationship with acute myocardial infarction.

Further, elastography and modulus imaging techniques generally use estimates of unknown strain or modulus parameters over a number of independent finite elements or image pixels distributed spatially over a region of interest. The higher the used spatial resolution for strain or modulus imaging, the larger the number of independent unknowns that should be estimated. As the parameter space grows, the search for parameter estimates that satisfy the desired objective functional becomes a difficult underdetermined problem. Typically, the number of unknowns far exceeds the number that can be uniquely determined from the underlying imaging data, resulting in many possible solutions satisfying the objective functional. In addition, large computational costs and computing time are generally incurred to probe parameter spaces of high-dimensionality (on the order of >100 dimensions).

Conventional methods for elastography and modulus imaging of biological tissue treat strain or modulus at each finite element or pixel of interest as independent unknowns, typically using a Levenburg-Marquardt or similar algorithm for optimization of the objective functional, as described in A. R. Skovoroda et al., "Tissue elasticity reconstruction based on ultrasonic displacement and strain images". IEEE Trans Ultrason Ferroelectr Freq Control, Col. 42,1995, pp. 747-765, and F. Kallel et al., "Tissue elasticity reconstruction using linear perturbation method", IEEE Trans Med Imaging, Vol. 15, 1996, pp. 299-313. To achieve robustness to local minima, multi-resolution methods have been used in which estimates are obtained on a low-resolution grid with fewer unknowns and these low-resolution estimates are then mapped to a higher-resolution grid to initialize parameter optimization in the full-resolution domain. These conventional methods can be time-consuming, requiring several minutes of processing for large regions of interest.

SUMMARY OF THE INVENTION

In contrast to the conventional techniques, an exemplary embodiment of a system, process and software arrangement according to the present invention is capable of determining a spatial distribution of strain and elastic modulus in at least one sample with high spatial resolution and sensitivity, while possibly simultaneously providing high-resolution images of structure and composition. The system, process and software arrangement according to the present invention are broadly applicable, and its capabilities are particularly relevant for biological tissues and vascular tissues.

In one exemplary embodiment of the present invention, OCT can be used to determine the structure and tissue composition of a vessel. This information may then be used to construct a numerical model representing the vessel and finite element modeling, using estimates of elastic moduli, can be subsequently used to predict the mechanical response of the vessel to a given stress load. Separately from this exemplary computation, an exemplary OCT elastography technique according to the present invention may be performed to measure the mechanical response of the vessel. The two pathways, modeling and imaging, can represent a) a prediction based on assumed elastic modulus distribution; and b) a measurement, respectively. The difference between these two results can be considered as an error function to be minimized by a modification of the initial estimate for the elastic modulus distribution. Through an iteration of this exemplary technique according to the present invention, the distribution and magnitude of elastic modulus can be determined. Such information could be displayed as a cross-sectional or three-dimensional image of elastic modulus. Additionally, by minimizing the error function, an improved elastographic image of strain can be generated. As a result, the exemplary embodiments of the system, process and software arrangement according to the present invention are capable of overcoming the limitations of current diagnostic technology wherein structure and/or strain are measured, and the biomechanical characteristics of the tissue remain unknown. Further, the present invention improves upon the resolution and sensitivity of previous methods for elastography.

In summary, the exemplary embodiments of the system, process and software arrangement according to the present invention allows for the simultaneous determination of structure, composition, strain and elastic modulus of samples for medical and non-medical applications.

In one exemplary embodiment of the present invention, a system, process and software arrangement are provided to determining data associated with at least one structural change of tissue. In particular, a first optical coherence tomography ("OCT") signal which contains first information regarding the tissue at a first stress level, and a second OCT signal which contains second information regarding the tissue at a second stress level are received. The first and second information are compared to produce comparison information. The data associated with the at least one structural change is determined as a function of the comparison information and further information associated with (i) at least one known characteristics of the tissue and/or (ii) characteristics of an OCT system.

For example, the structural change may be a strain of the tissue. In addition, the second stress can be different from the first stress. The further information may include a velocity distribution of the tissue, a mechanical characteristic (e.g., a compressability and/or elasticity characteristic) of the tissue, a tissue type, an optical characteristic of an imaging agent within the tissue, and/or a structure of the tissue. Further, the velocity distribution of the tissue may be determined based on a Doppler signal obtained from the tissue. the further information includes at least one of a velocity distribution of the tissue, a mechanical characteristic of the tissue, a tissue type, or a structure of the tissue.

According to another exemplary embodiment of the present invention, a method system and software arrangement are provided for determining data associated with at least one modulus of a tissue. For example, at least one optical coherence tomography ("OCT") signal which contains information regarding the tissue is received. Then, the modulus of the tissue is determined as a function of the received at least one OCT signal.

For example, the information can include a structure of the tissue and/or a composition of the tissue. The OCT signal may include a first OCT signal which contains first information regarding the tissue at a first stress level, and a second OCT signal which contains second information regarding the tissue at a second stress level, such that the second stress is different from the first stress. The first and second information may be compared to produce comparison information, such that the modulus is determined as a function of the comparison information. A numerical model can also be generated as a function of at least one of the first information and the second information. Further information regarding the tissue using the numerical model may be generated, the further information being associated with a response of the tissue to stress applied to the tissue.

The numerical model can be a dynamic numerical model, and the dynamic numerical model may include (i) constraints, (ii) a model complexity, and/or (iii) a model order which are modifiable as a function of the first information and/or the second information. The model complexity and/or a model order can be modifiable as a function of the first information and/or the second information. The dynamic numerical model can be executed to produce further information, and the further information may be provided to the dynamic numerical model so as to modify the constraints, the model complexity and/or the model order. The model complexity can include a plurality of model elements, at least first one of the elements can be associated with the elements based on weights of the first and/or second ones of the elements.

In addition, further data may be generated as a function of the comparison information and the further information. The numerical model may be modified as a function of the further data. Further, the modulus can be determined based on the numerical model. The strain information of the tissue may be obtained based on the numerical model. The comparison information can additionally be dependent on further information which is (i) at least one known characteristics of the tissue and/or (ii) characteristics of an OCT system. The further information can include a velocity distribution of the tissue, a compressibility/elasticity characteristic of the tissue, a tissue type, an optical characteristic of an imaging agent within the tissue. and/or a structure of the tissue. The velocity distribution of the tissue may be determined based on a Doppler signal obtained from the tissue.

Further, in contrast to conventional methods and techniques for biomechanical imaging, another exemplary embodiment of the present invention takes into consideration that tissues of the same type would likely have similar, and possibly almost identical, mechanical properties, and that high-tissue-contrast may be available in the OCT techniques for a segmentation of regions-of-interest into distinct tissue components (e.g., fibrous, lipid, calcified, etc.). This exemplary embodiment of the process according to the present invention can preserve the boundaries present between tissues, while reducing the parameter search space. For example, unlike estimation on a low-resolution grid, partial voluming of tissue types within each element can be minimized with this technique, allowing for sharp spatial gradients in strain or modulus to be preserved. In addition, an adaptive mesh refinement at elements where the biomechanical model poorly fits the data can be a contribution that is beneficial to the elastography and modulus imaging techniques.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION

Certain exemplary embodiments of the present invention can utilize a hybrid technique that combines an OCT technique with finite element modeling technique so as to determine structure, composition, strain and/or elastic modulus of samples.

Figure 1:
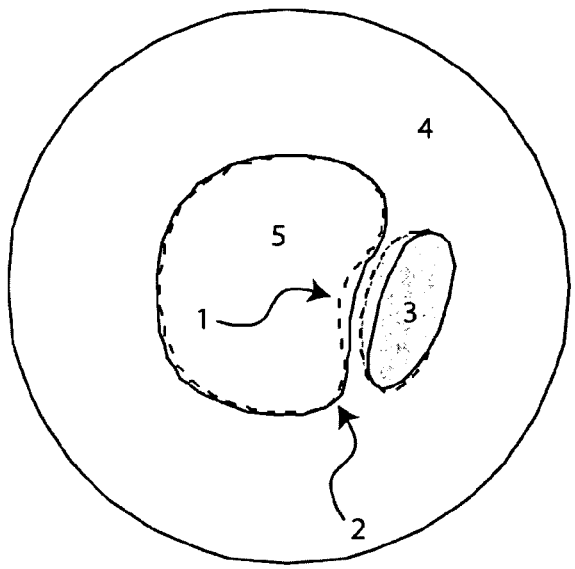
FIG. 1 is an exemplary schematic representation of a cross-section through a diseased vessel.

FIG. 1 illustrates an exemplary illustration of a diseased arterial cross-section consisting of a lipid pool 3 embedded within the normal vessel wall 4. Blood pressure variations within the lumen 5 can cause a deformation of vessel and plaque geometry. For example, in FIG. 1, dotted contours 1 deform to the location of the solid contours 2 as intraluminal pressure increases. Exemplary embodiments of OCT elastography techniques described herein are capable of not only tracking the displacement of boundaries within the vessel and plaque, but also estimating the biomechanical strains that arise within the tissue itself.

According to one exemplary embodiment of the OCT elastography technique according to the present invention, a velocity (e.g., magnitude and direction) of scatterers within a sample can be determined. In addition, an exemplary finite element modeling technique, based on the OCT structural image and estimates of tissue elastic modulus, may be used to predict a corresponding velocity distribution. The difference between these two exemplary distributions of velocity can be taken as an error function to be minimized by iterative optimization of the initial estimate of elastic modulus. The resultant distribution of elastic modulus can then be visualized in an image format. Further, the OCT elastography data can be used to graphically represent strain in an image format.

Figure 2:
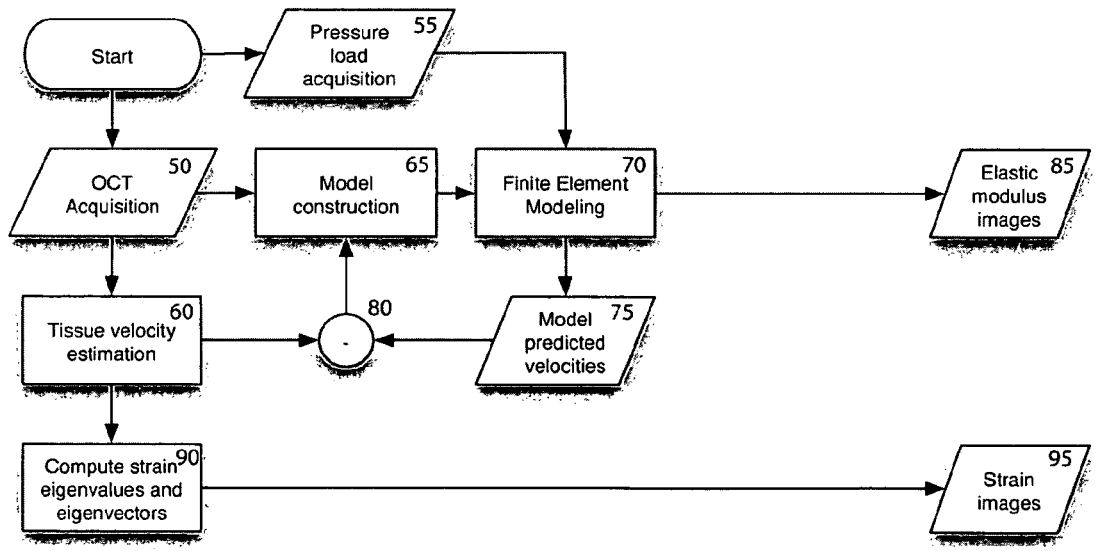
FIG. 2 is a generalized flow diagram of a combined OCT elastography—finite element exemplary modeling technique for determining elastic modulus distributions according to the present invention.

FIG. 2 graphically illustrates is a generalized flow diagram of a combined OCT elastography—finite element exemplary modeling technique for determining elastic modulus distributions according to the present invention, in separate steps. In the beginning of the process, OCT imaging and acquisition is performed in step 50, e.g., as the artery undergoes a dynamic deformation over the cardiac cycle. Simultaneously, the intraluminal pressure can be digitized and/or recorded with the corresponding OCT frame in step 55. The acquired OCT images from a single pressure level can form the basis for a geometric model for the diseased vessel in step 65 that may be meshed for a numerical simulation with finite element modeling (FEM) in step 70. Changes in the OCT image data as a function of time may be tracked with exemplary techniques for motion estimation so as to obtain a tissue velocity field in step 60. The corresponding strain eigenvalues and eigenvectors can then be computed or determined from the measured velocity field in step 90. The resulting images of tissue strain may be displayed as images in step 95.

In addition, estimated tissue velocities generated in step 60 can form the basis for model-based elastic modulus 70 determination. Applying the measured pressure load 55 and known boundary conditions to the finite element mesh initialized with a default distribution of modulus values, the numerical model may be executed to obtain a predicted velocity distribution in step 75. The model-predicted velocities obtained in step 75 may be compared with the measured velocities 60 by using the squared-error-measure technique in step 80. Based on the error generated by the comparison in step 80, the modulus values can be updated, and the model may be reconstructed in step 65, then re-simulated in step 70 to obtain a new set of predicted velocities. This process continues until the modulus estimates converge to a specified tolerance level. After convergence, the final exemplary elastic modulus distribution may be displayed as an image in step 85.

Figure 3:
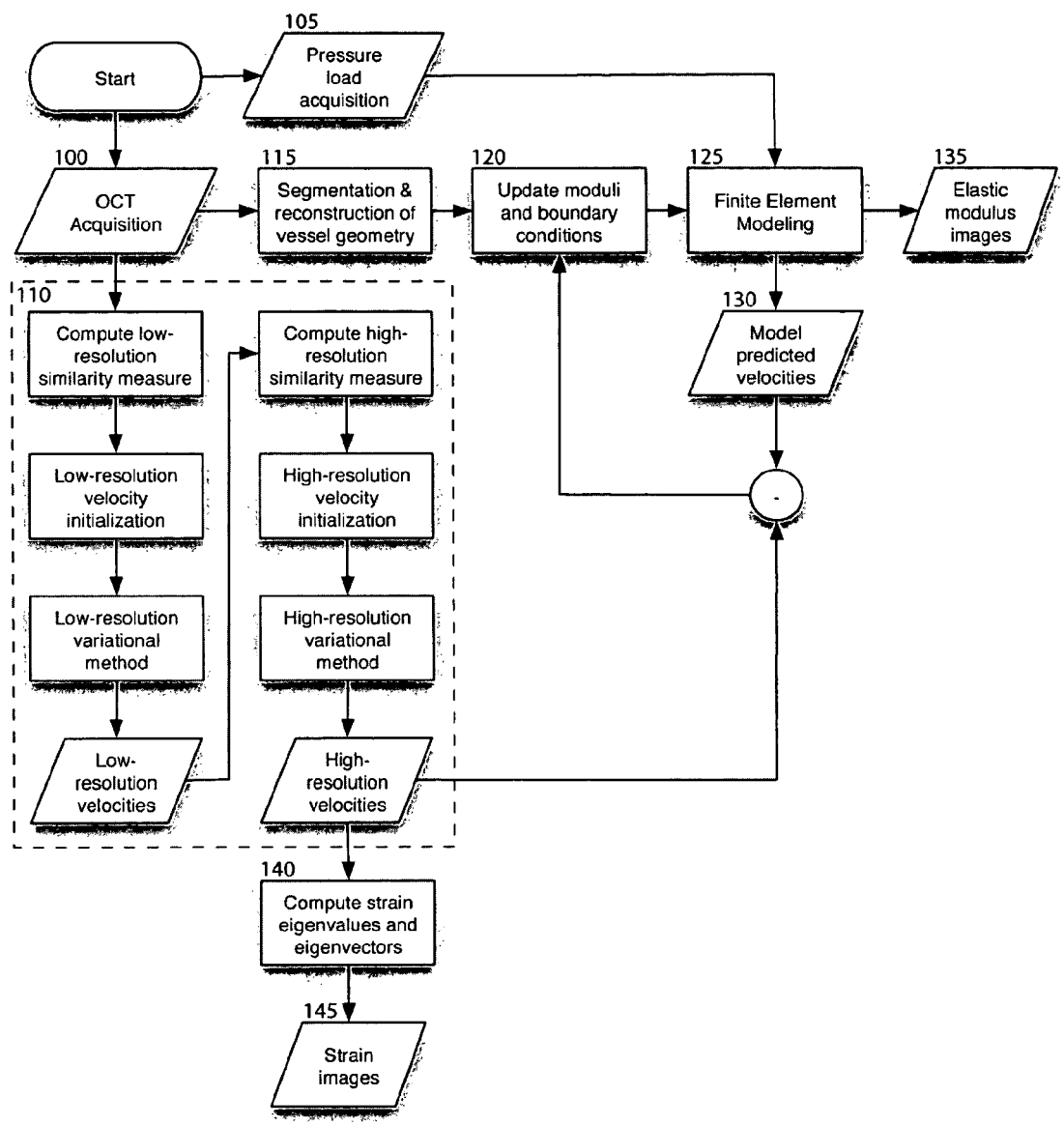
FIG. 3 is a flow diagram of an exemplary technique according to the present invention, which uses velocity distributions to determining the elastic modulus distributions.

FIG. 3 depicts a flow diagram of an exemplary technique according to the present invention, which uses velocity distributions to determining the elastic modulus distributions using an exemplary OCT technique. In particular, an OCT image acquisition (of step 100), and intraluminal pressure recording (of step 105) may be performed simultaneously. In this exemplary embodiment of the present invention, the dynamic OCT datasets can be processed using a multiresolution variational technique in step 110, the result of which may be a robust estimate of tissue displacement between two imaging time points. Tissue strain eigenvalues and eigenvectors may be determined from a velocity estimate in step 140, and then displayed graphically as images in step 145.

For an exemplary elastic modulus estimation, OCT data at a reference time point can be segmented to extract vessel and plaque surfaces in step 115. The surfaces may also be reconstructed in three-dimensions to define an arterial-specific geometry. This vessel geometry can then be meshed, boundary conditions applied, and mesh elements are assigned an initial modulus value in step 120 for a further use in a finite element modeling technique of step 125. This exemplary process/technique can lead to a set of tissue velocity predictions 130 that are used, together with the measured tissue velocities, to determine a squared-error-measure which drives the updating of elastic modulus values and boundary conditions used in the numerical model. The exemplary technique of modulus updating and numerical simulation continues iteratively to minimize the squared-error-measure and produce elastic modulus estimates that can converge to a specified tolerance level. A final elastic modulus distribution may be displayed graphically as an image in step 135.

In another exemplary embodiment of the present invention, an OCT technique may be performed to determine structure and composition in a sample while an applied stress is varied and measured. The OCT image acquisition rate is sufficiently high to avoid significant motion artifacts within individual images. The structure and composition determined for one value of the applied stress can be used to generate a numerical model representing the tissue and numerical modeling, incorporating the measured variation of stress and an initial estimate of elastic modulus distribution, is used to predict the structure for a second stress. An OCT image acquired at a corresponding second stress is compared with the predicted structure and the difference between the predicted and measured structure is minimized by iteratively optimizing the initial estimate of elastic modulus distribution. In this exemplary embodiment, numerical modeling, e.g., based on the optimized elastic modulus distribution, can be used for the final determination of both elastic modulus distribution and strain in a unified manner. These results can be graphically displayed in an image format.

In still another exemplary embodiment of the present invention, the OCT procedure may be performed to determine the structure and composition of a sample and, from this information, a numerical model representing the tissue is generated. Numerical modeling, based on an estimate of the elastic modulus distribution in the sample, can be used to predict the velocity distribution that would arise within the sample as a response to an applied stress. Additionally, the Doppler frequency shift arising from the reflection of the OCT beam from moving scatterers within the sample can be used in addition to the image intensity data to determine the depth resolved velocity distribution within the sample. The difference between the model prediction of velocity and the velocity measurements from OCT Doppler and image intensity data may be minimized by an iterative optimization of the initial elastic modulus distribution. The resultant distribution of elastic modulus can then be visualized in an image format. Independently, the Doppler OCT data can be used to graphically represent strain within the sample.

Figure 4:
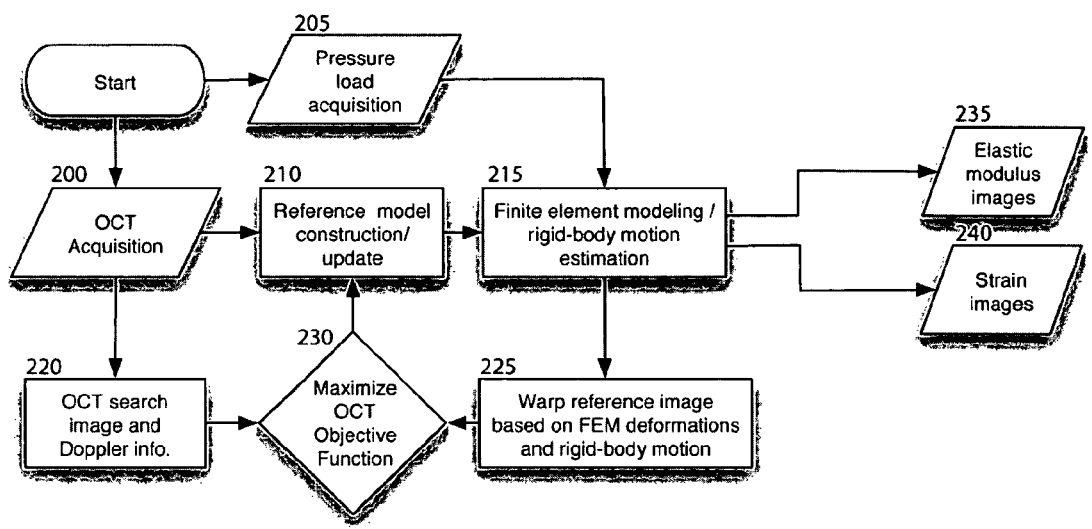
FIG. 4 is a flow diagram of another exemplary technique according to the present invention, which uses a structure and a structural deformation to determine the elastic modulus distribution and a strain distribution.

FIG. 4 graphically illustrates a flow diagram of another exemplary technique according to the present invention, which uses a structure and a structural deformation to determine the elastic modulus distribution and a strain distribution. An exemplary OCT imaging technique can be performed in step 200, and intraluminal pressure recording of step 205 may be performed simultaneously. The resulting data can be divided into search datasets with image and Doppler information in step 220, and a reference dataset which may be processed for numerical model construction in step 210. The reference geometry and pressure loads may then be used for joint finite element simulation and estimation of rigid-body motion of the model between reference and search datasets in step 215. The estimated rigid-body model transformation is combined with the model predicted mesh deformation to resample the reference intensity data in step 225, e.g., effectively warping it into the search dataset frame of reference. The warped reference data and measured search data may be combined within an OCT-specific objective function in step 230. The unknown modulus values can be updated in the model construction step 210 to maximize the objective function iteratively. Once convergence of the modulus estimates occurs, the corresponding modulus and strain distribution from the numerical model may be output and displayed graphically as images in steps 235, 240.

Optical Coherence Elastography

Optical coherence elastography can be preferably based on the same principles as those underlying ultrasound elastography. For example, as the tissue is imaged under mechanical loading, displacement occurs in image features that correspond to macroscopic architecture, e.g., tissue interfaces. In addition, motion can occur in coherent imaging speckle since the spatial distribution of microscopic tissue scatterers changes under loading. The estimation of motion from macroscopic architecture and microscopic speckle assumes that image features are well-preserved between consecutive images. The desired velocity estimate may therefore maximize similarity measures between blocks in a reference image and those in a search image acquired under different loading conditions.

Interference images obtained in OCT can be approximated by the product of an exponential decay term which models beam attenuation and a spatial convolution, $$I(x,y) = \exp(-2\bar{\mu}_s y)[\sigma_b(x,y) * h(x,y)] \quad (1)$$

Coordinates x and y correspond to lateral and axial scan directions, respectively oriented perpendicular and parallel to the sample beam axis. Parameter $\bar{\mu}_s$ is the mean attenuation due to scattering over the sample, $\sigma_b(x,y)$ models backscattering in the sample as a distribution of points with varying backscattering cross-sections, and h(x,y) represents the OCT system point spread function (PSF). The OCT PSF can be approximated as a separable and spatially invariant product between the source autocorrelation function, $\Gamma(y)$, and the pupil function, p(x), of the source-detection optics, $$h(x,y) = \Gamma(y)p(x) \quad (2)$$

For Gaussian beams, $$\Gamma(y) = \text{Re}[\langle E_s(y')E_s(y'+y)\rangle] = \exp\left(-\left(\frac{y}{2\Delta\sqrt{\ln 2}}\right)^2\right)\cos(2y/0) \quad (3)$$

and $$p(x) = \exp\left[-\left(\frac{Dx}{f_0}\right)^2\right] \quad (4)$$

where $E_s$ is the vector electric field amplitude of the source, o is the central free-space wavelength of the source, $\Delta$ is the FWHM spectral bandwidth of the source, f is the focal length of the objective lens, and D is the $1/e^2$ intensity diameter of the sample beam at the entrance pupil of the objective lens.

Based on this image formation model, a single point scatterer undergoing displacement from position $(x_0, y_0)$ in the reference image to a new position $(x_0+u, y_0+v)$ in the search image, will have corresponding reference and search interference images described by:

$$I_R(x,y) = \exp(-2\bar{\mu}_s y)[\sigma_b(x-x_0, x-y_0) * h(x,y)] \quad (5)$$
$$= \exp(-2\bar{\mu}_s y)[\sigma_b h(x-x_0, y-y_0)]$$

$$I_S(x,y) = \exp(-2\bar{\mu}_s y)[\sigma_b(x-x_0-u, x-y_0-v) * h(x,y)] \quad (6)$$
$$= \exp(-2\bar{\mu}_s y)[\sigma_b h(x-x_0-u, y-y_0-v)]$$

With conventional velocimetry, tissue motion is generally estimated by maximizing the correlation coefficient between sub-blocks of either the envelopes or complex magnitudes of equations (5) and (6). Each image can be subdivided into blocks of predefined size. For each reference block, cross-correlations with all search image blocks are computed to obtain correlation coefficients as a function of relative displacement between the reference and search locations. For example, according to one exemplary embodiment of the present invention, the best matching block in the search image will maximize the normalized cross-correlation function and the relative offset between this block and the reference provides the velocity estimate. This procedure is expressed mathematically in equations (7) and (8) for a reference position of (x,y) and M×N sub-blocks with mean intensities of $\mu_R$ and $\mu_S$. Overlapping sub-blocks can be used to estimate velocities on a finer grid in the reference image.

$$[\hat{u}(x,y)\hat{v}(x,y)] = \underset{[uv]}{\text{argmax}}_{x,y}(u,v) \quad (7)$$

$$_{x,y}(u,v) = \frac{\int_{-M/2}^{M/2}\int_{-N/2}^{N/2}[I_R(x'-x, y'-y)-\mu_R][I_S(x'-x-u, y'-y-v)-\mu_S]dx'dy'}{\left[\int_{-M/2}^{M/2}\int_{-N/2}^{N/2}[I_R(x'-x, y'-y)-\mu_R]^2 dx'dy' \int_{-M/2}^{M/2}\int_{-N/2}^{N/2}[I_S(x'-x-u, y'-y-v)-\mu_S]^2 dx'dy'\right]^{1/2}} \quad (8)$$

For the case of a translating impulse scatterer, velocity estimation with equations (5) through (8) can track the shift in the impulse response when $\bar{\mu}_s \approx \bar{\mu}_s(y+v)$. For real tissues containing ensembles of scatterers undergoing non-rigid deformation, the coherent impulse response from each scatterer produces interference patterns in the backscattered signal which would not likely to simply translate between sequential images in time. Velocity estimates can become more sensitive to interference "noise" which reduces the maximum achievable correlation coefficient in equation (8). Decorrelation effects such as those described above can occur whenever the correlation window size is large relative to the deforming structures of interest or when the strain induced by loading is large. In both cases, the effects of mechanical loading cannot be modeled by simple speckle translation since spatial distortion occurs in the underlying scatterer distribution. Under certain realistic circumstances, imaging noise and decorrelation not only reduce the correlation value at the true displacement within the correlation surface $_{x,y}(u,v)$, but also introduce jitter which shifts the location of correlation peaks in addition to multiple local maxima or false peaks whose values can exceed the correlation at the true displacement.

The 1-dimensional correlation between A-lines should ideally be a single, well-defined peak at the true displacement. However, due to speckle decorrelation and noise, multiple peaks are generally present in the correlation function, with the highest peak located at a velocity that is much lower than the true displacement. For the case of a 2-dimensional motion estimation, the ideal correlation function should also show a single well-defined peak, however, multiple local maxima can be present. For 2-dimensional estimates from images with features such as boundaries that extend over the entire correlation window, velocity components tangential to the boundary can also be difficult to determine. The correlation function in such a case does not contain a well-defined peak, rather correlation values are elevated over an broad range of displacements oriented tangentially to the boundary. For both the 1- and 2-dimensional cases, the resulting velocity estimates may lead to strain estimates that are excessively noisy for use in vascular OCE.

Robust Coherence Elastography

Strategies for improving velocity estimation can include image sequence blurring for noise suppression, the use of larger correlation windows, and smoothing of velocity fields after estimation by correlation maximization. Based on certain observations, these strategies can lead to certain improvements in velocity and strain estimates, but can also compromise the spatial resolution advantage of OCT for elastography. For example, image sequence blurring can remove not only noise, but also fine image features that may be useful in motion tracking. Large correlation windows may reduce an ability to track fine changes in the velocity field, and also can lead to a violation of the translating speckle model that is assumed in equations (7) and (8). Filtering of velocities or strains either with median-filters or other smoothing kernels operates on the measurements after they have already been made. Such approaches therefore may not be able to make use of information present within the underlying correlation functions to improve velocity and strain estimates. A more preferable approach to the estimation may allow for data-driven velocity filtering during the correlation maximization process itself. One such exemplary technique may be the variational technique as describe below.

The velocity estimation problem may be posed as a variational energy minimization in order to exploit velocity information present within the correlation functions while adding robustness to estimation by incorporating prior knowledge about velocity fields in the pulsating arterial wall. In this approach, we avoid image smoothing so as to preserve all available information from the full resolution data. An overall variational energy functional is $$E(V) = aE_D(V) + bE_S(V) + cE_I(V) \tag{9}$$

This energy depends on the unknown velocity field $V=[u\ v]$ and may be a weighted combination of three terms which control data fidelity, $E_D(V)$, strain field smoothness, $E_S(V)$, and arterial wall incompressibility, $E_I(V)$. The functional forms for each of these terms are:

$$E_D(V) = -\iint_{x,y}(V) dx dy \tag{10}$$

$$E_S(V) = \iint |\nabla^2 V|^2 dx dy \tag{11}$$

$$E_I(V) = \iint |\nabla \cdot V|^2 dx dy \tag{12}$$

where the expression $_{x,y}(v)$ in equation (10) is the correlation coefficient function shown in (8). Minimizing the data fidelity term in the absence of the strain smoothness and tissue incompressibility terms is the same as correlation function maximization and results in velocity estimates that are identical to those from conventional velocimetry. The strain smoothness and tissue incompressibility terms constrain velocity estimation to penalize deviations from prior knowledge about arterial tissue biomechanics. Information in correlation functions from neighboring reference locations is effectively combined to confer robustness to decorrelation, false peaks, and poorly-defined regions of elevated correlation coefficient values. The strain smoothness term forces the second derivative of the arterial velocity fields to vary smoothly over the wall whereas the incompressibility model couples the behavior of the u and v velocity fields so that points inside the wall do not deviate far from incompressibility. The desired velocity field estimate may minimize the overall variational energy:

$$\hat{V}(x,y) = \underset{V(x,y)=[u(x,y)v(x,y)]}{\mathrm{argmin}} \{aE_D(V(x,y)) + bE_S(V(x,y)) + cE_I(V(x,y))\} \tag{13}$$

In order to obtain a numerical solution to the energy minimization problem, we discretize the continuous expression in equation (13) to obtain:

$$\hat{V}(x,y) = \underset{V=\{uv\}}{\mathrm{argmin}} \{aE_D(V) + bE_S(V) + cE_I(V)\} \tag{14}$$

where the discrete velocity components in the column (x) and row (y) directions are represented respectively as the lexicographically-ordered column vectors $$u = \begin{pmatrix} \vdots \\ u_k[i_k, j_k] \\ \vdots \end{pmatrix}, \quad v = \begin{pmatrix} \vdots \\ v_k[i_k, j_k] \\ \vdots \end{pmatrix} \tag{15}$$

where k is the lexicographical index of the $k^{th}$ reference location of interest, $[i_k, j_k]$ are the row and column coordinates of this location within the reference image matrix $I_R[i,j]$. The discrete data fidelity term is:

$$E_D(V) = -\sum_k k[v_k, u_k] \tag{16}$$

where the correlation coefficient function in the discrete domain is $$k(v_k, u_k) = \frac{\sum_{m=-M/2}^{M/2} \sum_{n=-N/2}^{N/2} \{I_R[m-i_k, n-j_k] - \mu_R\}\{I_S[m-i_k-v_k, n-j_k-u_k] - \mu_S\}}{\left[\sum_{m=-M/2}^{M/2} \sum_{n=-N/2}^{N/2} \{I_R[m-i_k, n-j_k] - \mu_R\}^2 \sum_{m=-M/2}^{M/2} \sum_{n=-N/2}^{N/2} \{I_S[m-i_k-v_k, n-j_k-u_k] - \mu_S\}^2\right]^{1/2}} \tag{17}$$

for reference image $I_R[i,j]$ and search image $I_S[i,j]$ sampled from a regularly-spaced set of points defined on a rectilinear grid. In practice, to achieve rapid computation on the order of seconds for a full image, we use a fast normalized cross-correlation approximation that uses 2D FFTs to compute the numerator and pre-computed running sums for the denominator of equation (17). The discretized strain-smoothness and incompressibility terms are respectively $$E_S(V) = u^T D_{2r}^T D_{2r} u + u^T D_{2c}^T D_{2c} u + v^T D_{2r}^T D_{2r} v + v^T D_{2c}^T D_{2c} v \qquad (18)$$

$$E_I(V) = u^T D_{1r}^T D_{1r} u + v^T D_{1r}^T D_{1c} u + \\ u^T D_{1c}^T D_{1c} u + v^T D_{1r}^T D_{1r} v + u^T D_{1r}^T D_{1c} v + v^T D_{1c}^T D_{1c} v \qquad (19)$$

where $D_{2r}$ and $D_{2c}$ are second-order row- and column-difference matrices which operate on velocities from neighboring locations in column vectors u and v. Matrices $D_{1r}$ and $D_{1c}$ are the corresponding first-order row- and column-difference operators. In the case of lexicographically-ordered velocity vectors generated from 2D velocity fields defined on an M×N rectangular domain, the first-order row-difference operator $D_{1r}$ and first-order column-difference operator $D_{1c}$ are defined as follows:

$$D_{1r} = \begin{bmatrix} D1_{(M-1)N} & & \\ & \ddots & \\ & & D1_{(M-1)N} \end{bmatrix}, \qquad (20)$$

$$D1_{(M-1)N} = \begin{bmatrix} -1 & 1 & & & \\ & -1 & 1 & & \\ & & \ddots & \ddots & \\ & & & -1 & 1 \end{bmatrix}$$

$$D_{1c} = \begin{bmatrix} -I_M & I_M & & \\ & -I_M & I_M & \\ & & \ddots & \ddots \\ & & & -I_M & I_M \end{bmatrix} \qquad (21)$$

where $D1_{(M-1)N}$ is an (M−1)×N first-order difference matrix and $I_M$ is an M×M identity matrix. The corresponding second-order row-difference and column-difference operators are respectively $$D_{2r} = \begin{bmatrix} D2_{(M-2)N} & & \\ & \ddots & \\ & & D2_{(M-2)N} \end{bmatrix}, \qquad (22)$$

$$D2_{(M-2)N} = \begin{bmatrix} 1 & -2 & 1 & & \\ & 1 & -2 & 1 & \\ & & \ddots & \ddots & \ddots \\ & & & 1 & -2 & 1 \end{bmatrix}$$

$$D_{2c} = \begin{bmatrix} I_M & -2I_M & I_M & & \\ & I_M & -2I_M & I_M & \\ & & \ddots & \ddots & \ddots \\ & & & I_M & -2I_M & I_M \end{bmatrix} \qquad (23)$$

where $D2_{(M-2)N}$ is an (M−2)×N second-order difference matrix and $I_M$ is an M×M identity matrix.

To minimize equation (14), we derive its first variation to obtain the Euler equations $$a\frac{\partial E_D}{\partial u} + [b(D_{2r}^T D_{2r} + D_{2c}^T D_{2c}) + c(D_{1r}^T D_{1r} + D_{1c}^T D_{1c})]u + \\ cv^T D_{1r}^T D_{1c} u = 0 \qquad (24)$$

$$a\frac{\partial E_D}{\partial v} + [b(D_{2r}^T D_{2r} + D_{2c}^T D_{2c}) + c(D_{1r}^T D_{1r} + D_{1c}^T D_{1c})]v + \\ cu^T D_{1r}^T D_{1c} v = 0$$

where the first variations of the data fidelity terms are defined as $$\frac{\partial E_D}{\partial u} = \begin{pmatrix} \vdots \\ \frac{\partial_k[v_k, u_k]}{\partial u_k} \\ \vdots \end{pmatrix}, \frac{\partial E_D}{\partial v} = \begin{pmatrix} \vdots \\ \frac{\partial_k[v_k, u_k]}{\partial v_k} \\ \vdots \end{pmatrix} \qquad (25)$$

The Euler equations in formula (24) can be solved iteratively by forming the evolution equations, $$a\frac{\partial E_D[v^{t-1}, u^{t-1}]}{\partial u} + cD_{1r}^T D_{1c} v^{t-1} + Au^t = -(u^t - u^{t-1})/ \qquad (26)$$

$$a\frac{\partial E_D[v^{t-1}, u^{t-1}]}{\partial v} + cD_{1r}^T D_{1c} u^{t-1} + Av^t = -(v^t - v^{t-1})/$$

where $A = [b(D_{2r}{}^T D_{2r} + D_{2c}{}^T D_{2c}) + c(D_{1r}{}^T D_{1r} + D_{1c}{}^T D_{1c})]$ and is the time-step taken at each iteration. Rearranging to solve for the updated velocity estimate at time t, we obtain the matrix-vector equations $$u^t = (A+I)^{-1}\left(u^{t-1} - a\frac{\partial E_D[v^{t-1}, u^{t-1}]}{\partial u} - cD_{1r}^T D_{1c} v^{t-1}\right) \qquad (27)$$

$$v^t = (A+I)^{-1}\left(v^{t-1} - a\frac{\partial E_D[v^{t-1}, u^{t-1}]}{\partial v} - cD_{1r}^T D_{1c} u^{t-1}\right)$$

At steady-state, the time derivatives disappear and the resulting velocity estimates can satisfy equation (24). In practice, it is possible to begin from an initial guess for the velocity fields and solve for updated velocity estimates using LU decomposition at each iteration of equation (27). For non-integer velocity estimates, bicubic interpolation is used to compute the necessary gradients in the data fidelity term. This exemplary technique can continue until the maximum change in the velocity field magnitude is less than 0.01%.

Multiresolution Estimation for Convergence to a Global Minimum

Figure 5:
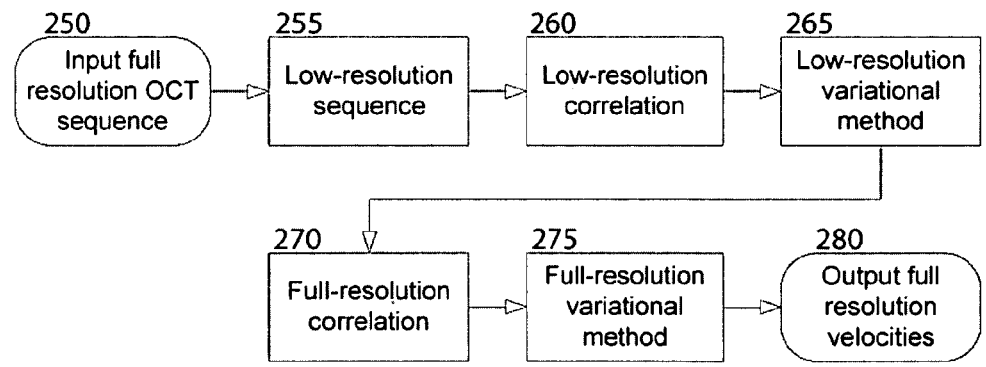
FIG. 5 is a block diagram of an exemplary technique for a multi-resolution velocity filed estimation according to the present invention.

The solution of equation (27) would likely converge to a local minimum in the variational energy function. The unknown velocity field should therefore be initialized close to the global minimum in order to ensure good global convergence properties. In order to achieve this, it is possible to use an exemplary multiresolution technique according to the present invention illustrated as a block diagram in FIG. 5. For example, the input full resolution reference and search images can first be downsampled by a factor of 10 to obtain a low-resolution sequence in step 255 from which an initial low-resolution estimate of the velocity field is obtained by correlation maximization in equations (7)-(8) in step 260.

This estimate may be used to initialize the variational method applied in the low-resolution domain in step 265. The robust low-resolution estimates of velocity may then be mapped into the high-resolution domain, and can be used to define the high-resolution search region for computing the full-resolution correlation functions at each reference position of interest in step 270. The low-resolution estimates from the variational method can also serve as a good initial guess for iterative estimation of velocity fields from the full-resolution correlation functions. The resulting full-resolution velocity estimates obtained in step 275 are then used for display and subsequent strain calculations in step 280.

Elastic Modulus Determination and Improved Strain Mapping

OCT-based tissue elasticity imaging which utilizes a unified computational framework (as shown in FIG. 4) for joint estimation of tissue elastic modulus and strain distributions consists of the following general procedure:

1. Numerical reconstruction from the reference OCT dataset (steps 210, 215).
   a. OCT segmentation and tissue classification.
   b. Initialization of modulus values and boundary conditions.
   c. Application of measured pressure load. The load may be intrinsic to the system under study, e.g. normal variation of intravascular pressure during the cardiac cycle, or may be externally controlled.
   d. Numerical simulation, finite element modeling (FEM) for example, to obtain predictions of vessel deformation
2. Estimation of rigid-body translation and rotation of the model between reference and search OCT image data (step 215).
3. Combination of rigid-body transformations and numerically predicted deformation field to warp the reference OCT dataset (step 225).
4. Calculation of an OCT-specific data fidelity term (step 230).
5. Update of elastic moduli and rigid-body transformations to maximize the OCT data fidelity and simulation of updated numerical model (step 210).
6. Display of final elastic moduli and strains after convergence of modulus vector estimates (steps 235, 240).

For example, the acquired reference OCT data can first be segmented to define the vessel wall geometry (step 210). Gradient-based active contours are used to extract the lumen boundary, which in vascular OCT imaging, exhibits a large intensity gradient magnitude. In the preferred embodiment, level-set-based active contours are used. In the level set approach, arterial surfaces are modeled as the zero level set of a higher-dimensional embedding space. For a closed planar curve, $C(p):[0,1] \to R^2$, the embedding surface, $u: \to R^2 \to R$, is represented by the signed distance function to the curve. The value assigned to each point in u is the signed distance to the closest point on curve C (points inside the curve are negative, while those outside are positive). To identify the curve that best fits an object boundary in an image, the following curve evolution equation is discretized and solved iteratively with gradient descent $$\frac{\partial \vec{C}}{\partial t} = \underbrace{g\kappa \vec{N}}_{\text{Curvature term}} - \underbrace{\left(\nabla g \cdot \vec{N}\right) \vec{N}}_{\text{Image-derived propagation term}} \quad (27A)$$

where g is a function of the image gradient magnitude, $\kappa$ is the Euclidean curvature, and $\vec{N}$ is the unit normal. The curvature term causes the curve to become smooth except in the presence of strong image gradients, whereas the image-derived curve propagation term pulls the curve towards strong gradients at object boundaries. Since u is an implicit representation of C, solving (28) is equivalent to solving:

$$\frac{\partial \vec{u}}{\partial t} = \underbrace{g\kappa |\nabla u|}_{\text{Curvature term}} + \underbrace{\nabla g \cdot \nabla u}_{\text{Image-derived propagation term}} \quad (27B)$$

and then selecting the zero level set to extract the curve C. The level set evolution equation in (27B) is topologically flexible and accommodates complex changes in vessel branching automatically. Entropy-satisfying upwind finite differencing is used together with a narrow-band update technique as described in to solve (2) with numerical stability and speed.

The outermost boundary of the vessel wall in the OCT data may be defined based on intensity thresholding and computational geometry. The imaging data are first thresholded to locate all points with signal intensity exceeding the measured noise floor of the OCT system. As understood by those of ordinary skill in the art, a geometric convex hull can then be formed from these points and the resulting surface is used to define the outer vessel boundary.

OCT voxels falling within the inner and outer vessel surface are then assigned to regions of lipid-rich, fibrous, or calcific tissue based on supervised Maximum A Posteriori (MAP) classification and experimentally-derived class-conditional intensity probability density functions. In an exemplary embodiment of the present invention, training data from OCT and histology are registered, then regions of lipid-rich (L), fibrous (F), and calcified (C) tissue are located in the OCT data based the corresponding histology data. For each of the tissue classes, OCT image intensity values are extracted to generate frequency histograms that approximate the class-conditional intensity probability distributions. This process results in three class-conditional probability distributions for the OCT intensity, I, at any given voxel: P(I|F), P(I|L), and P(I|C). Using Bayes formula, the probability that a voxel belongs to tissue class F, L, or C, given its intensity value g is given by the equations:

$$P(F|I) = \frac{P(I|F)P(F)}{P(I)}; P(L|g) = \frac{P(I|L)P(L)}{P(I)}; \quad (27C)$$

$$P(C|I) = \frac{P(I|C)P(C)}{P(I)} \text{ where}$$

$$P(I) = P(I|F)P(F) + P(I|L)P(L) + P(I|C)P(C)$$

The prior tissue class probabilities P(F), P(L), P(C) can be derived from in vivo observations about the frequency of each lesion type and it is assumed that these observations also hold on a per voxel basis. From the class-conditional probability values, the probability of classification error associated with assigning a given tissue class to a voxel is computed. The tissue assignment that leads to the lowest probability of classification error is selected for the voxel tissue class.

Following segmentation and classification, surfaces may be obtained which define vessel geometry and interfaces between intra-plaque voxels with similar elasticity. As is understood in the art, these surfaces are then used to construct a finite element model in any commercially available or custom-coded finite element analysis program. With this program or alternate mesh generation procedure known in the art, a finite element mesh of the vessel and intraplaque components is generated. Boundary conditions are applied by defining a fixed point on the lumen contour at the arterial inlet and a point on the opposite side of the lumen centroid that is free to translate in the radial direction. The measured pressure load may be applied to the lumen surface of the vessel model and initial elastic modulus estimates are assigned to each mesh element based on the results of OCT tissue classification (in the corresponding image region) and average modulus values for lipid, fibrous, and calcified tissue from the vascular biomechanics literature.

In one exemplary implementation of the technique according to the present invention, each mesh can consist of either 2-dimensional quadrilateral or 3-dimensional isoparametric linear elastic finite elements depending on whether the input OCT data are 2-dimenisonal images or 3-diomensional volumes. Either displacement-based (u) elements or displacement/pressure (u/p) based elements can be used to avoid 'locking' as the Poisson ratios approach 0.5. The unified framework for OCT tissue elasticity imaging is not limited however to the use of these specific structural elements or constitutive material models. For example, non-linear Mooney-Rivlin strain energy functions can be substituted for the linear material model used in the current embodiment. Following model construction, finite element simulations are run to predict the nodal positions of the deformed mesh in the search OCT dataset.

Rigid-body translation and rotation can occur in the vessel between the reference and search images and the FEM model as described does not reflect this due to the applied boundary conditions. Therefore, standard methods for multi-dimensional image correlation as known in the art are used to compute the rigid-body translation and rotation of the finite element model between the reference and search datasets. The estimated rigid-body transformation is then applied to the FEM-predicted mesh deformation to obtain the overall behavior of the finite element model between the reference and search datasets (see step 215).

The nodal displacements of the FEM can mesh as it undergoes rigid-body motion and deformation define a warping field that maps spatial coordinates in the reference data to predicted locations in the search dataset. This warping field is used to spatially resample the OCT reference imaging data with multidimensional interpolation (225). In the preferred embodiment, linear interpolation kernels are used due to their simplicity and computational speed. In principle however, any multidimensional interpolation procedure such as spline or cubic interpolation could be used instead.

The resulting warped reference data can be used together with the search data and OCT Doppler measurements to compute an OCT-specific objective function defined by a linear combination of the following terms (see step 230):

1. the negative sum-of-squared-differences between intensities in the warped reference image and the measured OCT data in the search image;
2. the normalized mutual information between the intensities in the warped reference imaging and the measured OCT data in the search image;
3. the sum over the elements of the correlation coefficient between intensities in the warped reference imaging and the measured OCT data in the search image;
4. the sum over the nodes of the squared-error between a model-predicted and measured change in optical properties within the tissue or bound imaging agent due to the applied pressure/displacement load; and
5. the sum over the nodes of the dot-product between Optical Doppler velocity measurements and FEM-predicted displacements in the direction of the imaging beam.

This exemplary objective function is iteratively maximized by first updating the elastic moduli and rigid-body transformation parameters, and then re-running the FEM model at each iteration to obtain improved predictions of vessel deformation between the reference and search frames. As understood by those of ordinary skill in the art, a multidimensional constrained conjugate-gradient technique can be used to maximize the overall objective function. Constraints in this exemplary technique may be imposed to limit the range of possible modulus values for each element based on the biomechanical behavior (measured a priori from biomechanical testing) typical of the tissue class assigned to the element based on the OCT image intensity. This procedure for constrained function maximization represents one of a number possible techniques that could be substituted instead. In one exemplary implementation of the present invention, the estimation procedure can be considered complete when an absolute change in the maximum modulus value falls below 0.0001. At convergence, the final modulus distribution and corresponding strain and stress fields from the corresponding finite element simulation may be displayed as a color-mapped image or volume rendering depending on the dimensionality of the input data (235, 240).

Autoranging

The present invention can also use autoranging technology, including processing techniques, as described in copending U.S. application Ser. No. 10/136,813, filed Apr. 30, 2002, the entire disclosure of which is incorporated herein by reference.

The autoranging mechanism may, in one exemplary embodiment, allow the techniques of the present invention to be applied to vascular imaging, such that the imaging catheter is not required to be centered within the vascular lumen. In this exemplary embodiment, the feedback signal of the autoranging mechanism should preferably be incorporated into the imaging mechanism of the present invention, e.g., to facilitate and preserve an accurate determination of vascular structure.

EXAMPLE

Figure 6:
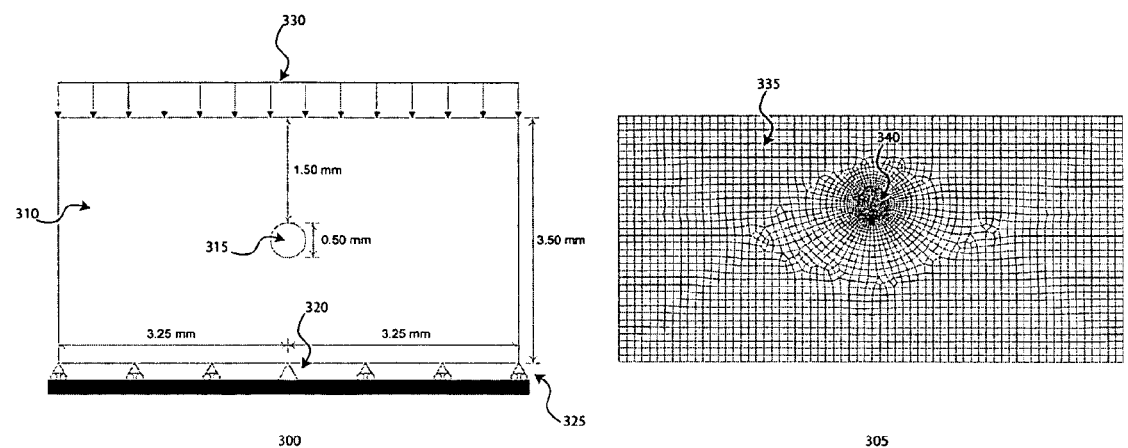
FIG. 6 is an illustration of an exemplary finite element geometry and finite element mesh, respectively, used in experiments so as to verify results of the exemplary embodiment of the present invention.

The following description provides details on the experimental testing of an exemplary embodiment of the method according to the present invention: In particular, the exemplary multi-resolution variational method was performed in simulated OCT imaging during axial compression of a tissue block containing a circular inclusion. FIG. 6 depicts a finite element model geometry 300 and corresponding finite element mesh 305 used for the tissue block and circular inclusion. Sequential interference images were generated as described in equations (1)-(6) by computing the product of an exponential decay term and a convolution between the coherent OCT point-spread function and the distribution of backscattering arising from point scatterers moving in the sample.

Backscattering values at discrete points within the tissue block were simulated as independent uniform random variables with a variance of 10 for scatterers within the block and a variance of 2 for scatterers within the circular inclusion. These values were empirically chosen to produce higher mean backscattering within the block relative to the inclusion. The resulting contrast difference emulates that observed between lipid and the normal arterial wall in OCT images.

Motion of the tissue scatterers during compression was simulated using displacement fields from finite element modeling of the tissue geometry. A two-dimensional rectangular geometry 310 with an embedded circular inclusion 315 was defined. The inclusion diameter in all simulations was 500 μm.

Fixed-point boundary conditions were imposed at the center of the bottom edge of the block 320 and roller boundary conditions were assigned at all other points on the bottom edge 325. An axial (downward) displacement-load was applied to the top surface 330 so that the block was compressed by 0.15 mm over 5 time steps, to achieve an overall strain of 4.3%. With each time step, the load induced ~0.9% strain within the block.

Both the block and inclusion were modeled as nearly incompressible linear elastic materials (v=0.495). For all simulations, the block was assigned unit elastic modulus, while the inclusion modulus was varied to represent a lipid rich or calcific lesion embedded in fibrous tissue. The modulus ratio of lipid to fibrous plaque is approximately 0.0001, and the modulus ratio of calcium to fibrous plaque is approximately 5. Finite element modeling was performed using ADINA 8.0 (Watertown, Mass.), with a mesh 335, 340 composed of 9-node, quadrilateral, 2D, plane strain elements. The mesh density, defined by the edge length of each element, was 0.025 mm in and around the inclusion 340 and 0.1 mm in the surrounding block 335. Each simulation model consisted of approximately 3200 elements and 13000 nodes. The displacement fields computed at each time step were used to represent tissue scatterer velocities, u(x,y) and v(x,y), between sequential OCT frames. The backscattering field, $\sigma_b(x,y,t+1)$, associated with moving tissue scatterers at time t+1 was computed using the equation $$\sigma_b(x,y,t+1)=\sigma_b(x-y(x,y),y-v(x,y),t) \quad (28)$$

In practice, the tissue scatterer field in the first frame may be first upsampled, and then non-uniformly resampled with linear interpolation in equation (28) to obtain tissue scatterer fields in sequential frames.

Figure 7:
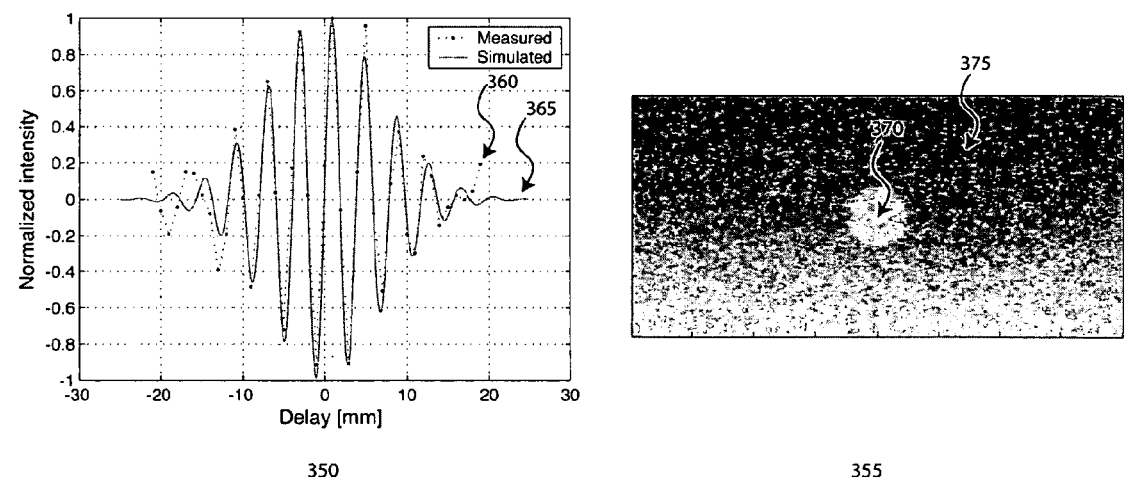
FIG. 7 is an exemplary illustration of a simulated OCT point-spread-function with a fringe-resolved measurement, and a simulated OCT image of an inclusion within a tissue block.

Using the coherent PSF approximation in equations (2)-(4), it is possible to simulated a PSF based on measurements of the axial fringe pattern of our OCT system. FIG. 7, a graph 350 illustrates measurements of the fringe-resolved OCT point spread function (PSF) 360 relative to the simulated OCT PSF 365. Simulations and measurements are have certain matching characteristics. Convolution of this coherent PSF with tissue scatterer fields from equation (28) was followed by multiplication with an axial exponential decay and downsampling to obtain a sequence of simulated images I(x, y,t) with a pixel size of 1 μm by 25 μm. The degree of speckle or multiplicative noise present in these simulations was further controlled by using the noise model $$I_n(x,y,t)=I(x,y,t)+nI(x,y,t) \quad (29)$$

where n is a uniformally-distributed random variable with zero mean and variance $\sigma_n^2$. FIG. 7 355 demonstrates the result of demodulating a simulated OCT image generated from the FEM geometry in FIG. 6 300 and the OCT PSF 365. The inclusion 370 is visible within the tissue block 375 and has an appearance that approximates that of a lipid pool within the normal arterial wall.

The methods described herein can be implemented using C++ programming language for rapid processing, and visualization and analysis may be performed in MATLAB (MathWorks, Natick, Mass., USA). To achieve rapid computation on the order of seconds for a full image, we used a fast normalized cross-correlation approximation to the correlation coefficient function in equation (8) that uses 2D FFTs to compute the numerator and pre-computed running sums for the denominator.

For conventional velocity estimation techniques based on correlation maximization, each correlation function was upsampled with bi-cubic interpolation by a factor of 50 around the peak in order to detect sub-pixel shifts of 0.02 μm axially and 0.5 μm laterally. A reference block size of 81×7 pixels (81×175 μm) and a search region of 361×21 pixels (361×525 μm) were used to compute correlation functions for the conventional method. These parameters were empirically determined to balance the need for sensitivity to spatial variations in velocity against the need to minimize errors in velocity estimation. Median filtering of velocity and strain estimates from conventional motion tracking was performed with a 5×5 kernel prior to comparisons with results from the exemplary variational approach according to the present invention.

For the low-resolution step of the exemplary embodiment of the variational method, a reference block size of 15×11 pixels (75×1375 μm) and a search region of 61×41 pixels (305×5125 μm) were used to compute each correlation function. At full-resolution, a reference block size of 25×7 pixels (25×175 μm) and a search region of 101×21 pixels (101×525 μm) were used. Weighting parameters for the variational approach were empirically determined to be a=1, b=20, and c=0.1 based on a subset of simulated OCT sequences. These values were then used for velocity estimation in the OCT experiments described below.

Following velocity estimation, the deformation matrix F was calculated at every point in the velocity field using first-order finite difference approximations to the expression $$F = \begin{bmatrix} 1+\frac{\partial u}{\partial x} & \frac{\partial u}{\partial y} \\ \frac{\partial v}{\partial x} & 1+\frac{\partial v}{\partial y} \end{bmatrix} \quad (30)$$

The deformation matrix is related to the strain matrix E and the identity matrix I by the relationship $$E = \begin{bmatrix} xx & xy \\ xy & yy \end{bmatrix} = \frac{1}{2}(F^T + F - 2I) \quad (31)$$

if a small strain approximation is assumed. For simulated OCT imaging of axial compression, we present results for the axial strain component $_{yy}$ of the strain matrix whereas for imaging experiments with lateral stretching, we present results for the lateral strain component $_{xx}$. Errors in velocity and strain field estimates were evaluated based on the normalized root-mean-squared error measures $$RMS_{velocity} = \sqrt{\frac{1}{N}\sum_{k=1}^{N}\left(\frac{v_k - v_{k,real}}{v_{k,real}}\right)^2} \quad (32)$$

$$RMS_{strain} = \sqrt{\frac{1}{N}\sum_{k=1}^{N}\left(\frac{k-k,real}{k,real}\right)^2}$$

where N is the total number of estimates, $v_k$ and $V_{k,real}$ are the estimated and real axial or lateral velocities, and $_k$ and $_{k,real}$ are the estimated and real axial or lateral strains at the $k^{th}$ point of interest within the velocity field.

Simulation Experiments

The detectability of a 500 μm inclusion were examined as a function of speckle decorrelation and compared the RMS error in axial velocity and strain estimates from conventional motion estimation relative to those from robust estimation. Values for $V_{k,real}$ and $_{k,real}$ were obtained directly from finite element modeling. Velocities were reported in units of pixels with positive axial and lateral velocities corresponding respectively to downward and rightward displacement.

Figure 8:
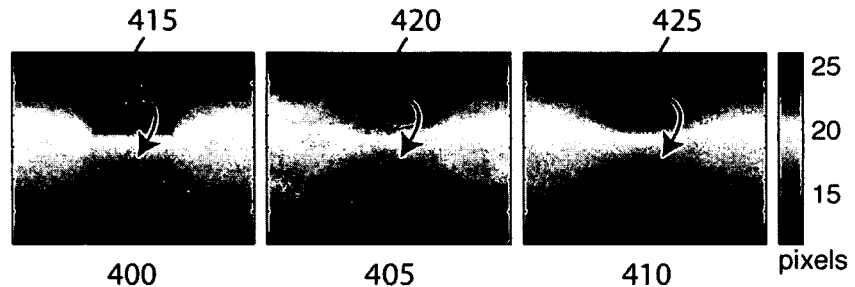
FIG. 8 is an exemplary illustration of axial velocity fields for a compliant inclusion according to the exemplary embodiment of the present invention, in which frame (400) designates exemplary true axial velocities from finite element modeling, frame (405) designates exemplary axial velocity estimates from conventional motion tracking; and frame (410) designates exemplary axial velocity estimates from an exemplary multi-resolution variational technique.
Figure 9:
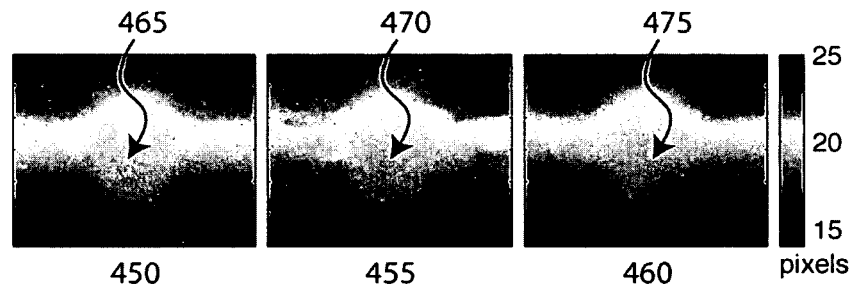
FIG. 9 is an exemplary illustration of axial velocity fields for a stiff inclusion, with frames (450), (455) and (460) corresponding to the image representations of similar frames in FIG. 8.

FIGS. 8 and 9 illustrate the FEM-derived axial velocity fields 400, 450 corresponding respectively to the compliant and stiff inclusion movie sequences. In addition, they show the axial component of velocity measurement results from conventional motion tracking 405, 455 and robust estimation within the variational framework 410, 460. For these examples, the inclusion location corresponds to labels 415, 420, 425, 465, 470, and 475. The estimated velocity fields from both methods are qualitatively similar to the true velocity from FEM. The estimate from the variational approach appears significantly smoother than that from conventional tracking. Additionally, the axial velocity RMS error is greater from conventional velocimetry than from robust estimation. For the stiff inclusion, the RMS error in the axial velocity field was 1.60% from conventional velocimetry whereas the RMS error with robust estimation was 1.04%. Similar results were obtained from the compliant inclusion (1.83% for the conventional approach vs 1.40% for the variational approach).

Figure 10:
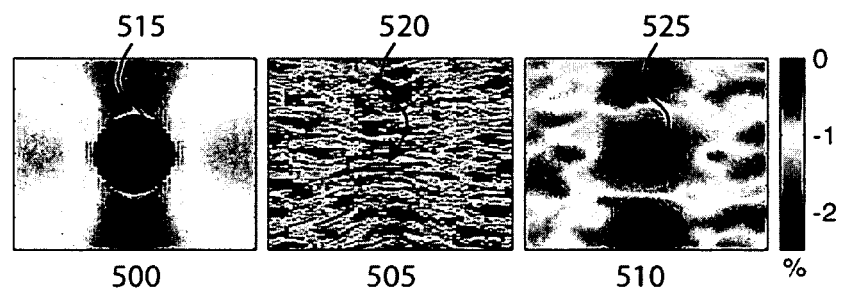
FIG. 10 is an exemplary illustration of axial strain fields for a compliant inclusion, with frames (500), (505) and (510) corresponding to the image representations of similar frames in FIGS. 8 and 9.
Figure 11:
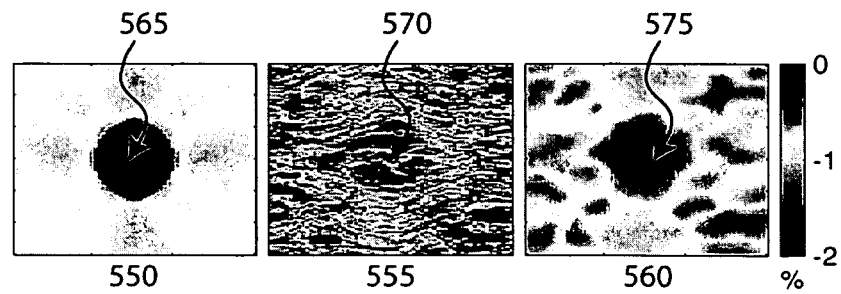
FIG. 11 is an exemplary illustration of the axial strain fields for a stiff inclusion, with frames (550), (555) and (560) corresponding to the image representations of similar frames in FIGS. 8, 9 and 10.

FIGS. 10 and 11 show the corresponding axial strain fields for the compliant and stiff inclusion simulations respectively. Frames 500 and 550 designate the true axial strain from finite element modeling; frames 505 and 555 designate the axial strain estimates from conventional motion tracking; and frames 510 and 560 designate the axial strain estimates from the multi-resolution variational method. The inclusion location in these images corresponds to labels 515, 520, 525, 565, 570, and 575.

The effect of velocity noise on strain field measurements is evident from these examples. While estimates from conventional and robust velocimetry were both qualitatively similar to the FEM-derived displacements, the strain estimates are less similar to the true strain. Axial strain is the derivative of the axial velocity field, therefore any noise present in the velocity estimate is accentuated in the strain image due to the high-pass characteristics of the derivative operator. Even with median-filtering, it is difficult to fully appreciate the extent and magnitude of the strain difference within the inclusion for strains derived from conventional motion tracking. In contrast, it is possible to determine the location and size of the inclusion with robust strain estimation. Furthermore, it is possible to visually distinguish the compliant inclusion from stiff inclusion with the variational approach. Quantitatively, the difference in RMS strain error between the conventional and variational methods is marked. In the stiff inclusion, for example, with the conventional approach, the RMS strain error is 109.1% whereas with the variational method, RMS strain error is 27.5%. Strains derived from conventional tracking are challenging to interpret whereas robust estimation allows for easier and more accurate interpretation of strains measurements for comparisons between lesion types.

Imaging Experiments

Light from a broadband optical source with a center wavelength of 1310 nm and a bandwidth of 70 nm is split into a reference and sample field within an interferometer. The sample field is focused through the scanning optics to probe tissue at a depth corresponding to the optical path length of the reference arm. Backscattered light returning from the sample arm mixes with the reference field to produce an interference signal that is digitized to produce pixels that are 1 μm (axial) by 25 μm (lateral). The amplitude of the interference signal carries information about tissue structure and optical properties at the scan depth defined by the reference arm. Tissue structure in an XY cross-section is probed in the axial (Y) direction by varying the optical path length of the reference arm and in the lateral (X) direction by sweeping the sample beam across the specimen. In this exemplary manner, image frames consisting of 2500 axial pixels by 500 lateral pixels are acquired in 250 ms.

A normal segment of human aorta harvested from autopsy was warmed to 37° C. in phosphate buffered saline. Imaging was performed within 24 hours of harvesting. The cylindrical aortic segment was sectioned longitudinally and opened to obtain a rectangular tissue specimen with the luminal surface exposed to the sample beam. The longitudinally cut ends were affixed to a sample holder so that mechanical loading in the lateral direction would approximate circumferential stretching of the intact aortic segment. The specimen was mounted horizontally within the sample holder so that one end was rigidly fixed while the other end was affixed to a micromanipulator that allows for one-dimensional translation along the horizontal axis. The imaging position within the sample was monitored by visualizing an aiming beam (laser diode, 635 nm) that was coincident with the sample beam. Scans were positioned within the center of the specimen and the scan direction within the sample arm was aligned so that scatterer displacements were confined within the imaging plane.

In these imaging experiments, velocity and strain estimations have been examined in a normal aortic specimen under either static or lateral stretching conditions. For the static case, the ground-truth velocity and strain fields should both be zero. Therefore, the deviation of velocity and strain estimates away from zero was determined as one measure of performance. For the case of lateral stretching, the expected strain distribution is homogenous and we report the standard deviation of estimated strains as a measure of strain homogeneity within the sample.

Under static conditions, the estimated mean lateral velocity with the conventional approach was −0.17 μm per frame compared with a nominal applied translation of 0 pixels per frame. The standard deviation of the lateral velocity estimates over the field was 3.94 μm per frame. In the axial direction, the mean and standard deviation were 0.66 μm and 4.28 μm, respectively. Velocity estimation with the variational approach showed a mean velocity of 0.0017 μm per frame laterally (0.54 μm per frame axially), which was closer to the applied translation than the results from the conventional method. The velocity standard deviation of 0.16 μm per frame laterally (0.58 μm per frame axially) was also smaller than for the conventional method results.

The mean and standard deviation of strain estimates over the field were respectively −0.043% and 5.5% laterally (−0.24% and 11.26% axially) for the conventional approach, compared with a nominal applied strain of 0% over the field. In contrast, robust estimation generally provides better strain estimation performance. The mean and a standard deviation of strain estimates were −0.0038% and 0.12% laterally (−0.024% and 0.12% axially), respectively.

Figure 12:
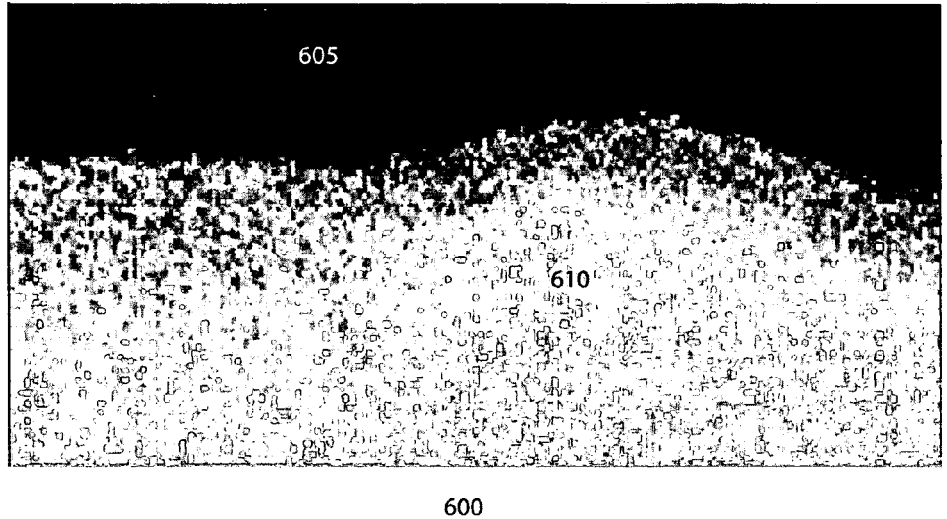
FIG. 12 is an exemplary OCT image of an aortic specimen.
Figure 13:
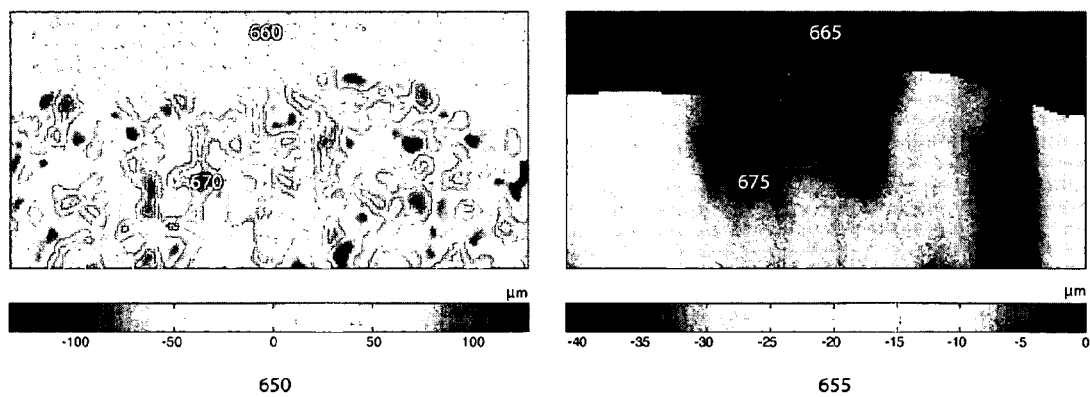
FIG. 13 is an illustration of an exemplary lateral velocity distribution for the aortic specimen of FIG. 12 undergoing a lateral stretch.
Figure 14:
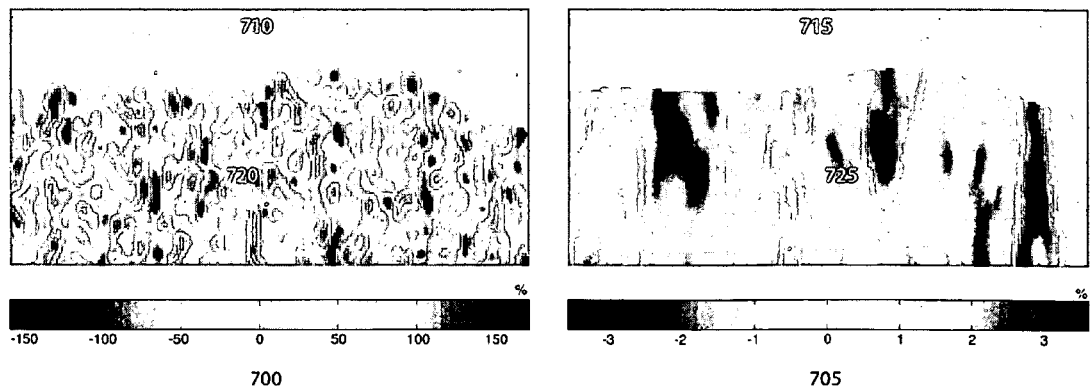
FIG. 14 is another illustration of an exemplary lateral strain distribution for the aortic specimen of FIG. 12 undergoing a lateral stretch.

An exemplary OCT image of an aortic segment undergoing lateral translation with slight lateral stretching is shown in FIG. 12 as illustration 600. The region labeled 605 has been masked out and corresponds to air above the surface of the aortic tissue 610. FIG. 13 illustrates a lateral component of the velocity field measurement. Frame 650 has been generated from the conventional velocity estimation method and frame 655 using an exemplary embodiment the variational technique according to the present invention. The regions 660 and 665 corresponding to air above the tissue have been masked out and the regions 670 and 675 correspond to aortic tissue. FIG. 14 illustrates the lateral component of the estimated strain field. Frame 700 was generated from the conventional method and frame 705 an exemplary embodiment the variational technique according to the present invention. The regions 710 and 715 corresponding to air above the tissue have been masked out and the regions 720 and 725 correspond to aortic tissue.

Velocities from robust estimation were observed to vary more smoothly in both the lateral and axial directions than estimates from conventional estimation. For the conventional approach, the strain mean and strain standard deviation were 0.22% and 47.26% in the lateral direction and −3.46% and 85.08% in the axial direction. In contrast, the strain field from robust estimation showed a mean and a standard deviation of −0.026% and 1.32% in the lateral direction and 0.02% and 0.14% in the axial direction. These results indicate that estimates from robust strain measurement are more consistent with the expected homogeneous strain field than those from conventional strain measurement.

Figure 15:
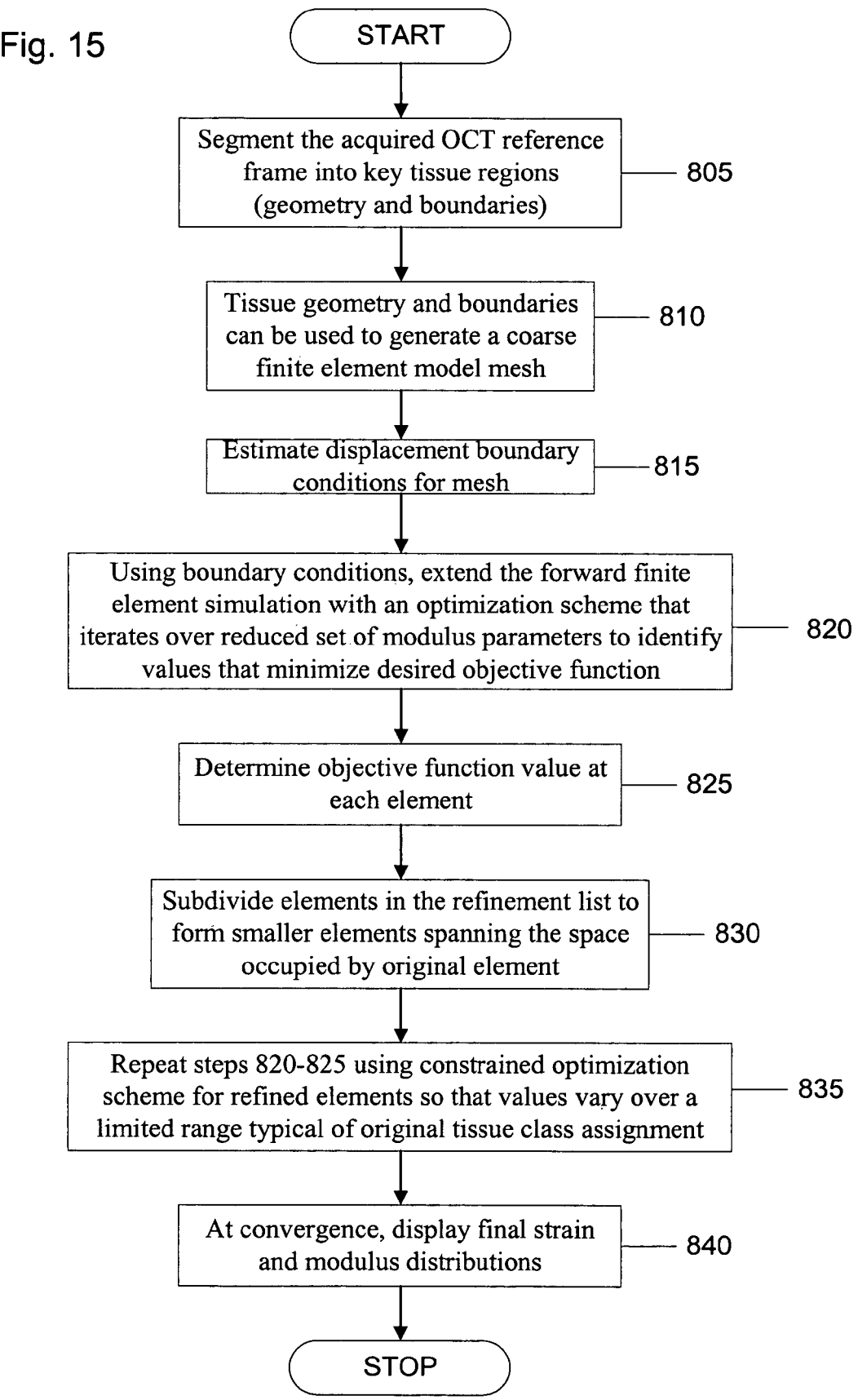
FIG. 15 is an exemplary flowchart of another exemplary embodiment of a method in accordance with the present invention for an OCT-based estimation of biomechanical properties that can be used for an efficient parameter reduction.

In accordance with yet another exemplary embodiment of the present invention, an exemplary framework is provided for OCT-based estimation of biomechanical properties that can be used for an efficient parameter reduction strategy. Such strategy can assist with rapid, intraoperative estimates while preserving sharp gradients in mechanical properties that may be present in the underlying data. There is typically a trade-off between parameter reduction and spatial resolution. It is preferable to reduce or minimize this trade-off, and improve computational performance by using the soft-tissue-contrast of OCT to discriminate between tissue regions, and by the knowledge that tissues of the same type have similar mechanical behavior. One exemplary embodiment of a method according to the present invention to achieve this is shown in FIG. 15 can be as follows:

a. Segment the acquired OCT reference frame into key tissue regions (step 805). The segmentation can be automated based on clustering regions with similar mean intensity, intensity variance, slope as a function of A-line depth, or other candidate intensity metric. The number of distinct regions can be the number of unknown parameters to be estimated, e.g., may be on the order of 2-6 unknowns.

b. The tissue geometry and boundaries identified in step 810 can be used to generate a coarse finite element model mesh (step 810). Since tissue boundaries are used as input to the meshing step, no elements should straddle more than one tissue type. Each element belongs to one tissue type and will be assigned to the corresponding unknown modulus for that tissue.

c. Estimate displacement boundary conditions for the mesh (step 815).

d. Using the boundary conditions from step 815, extend the forward finite element simulation with an optimization scheme that iterates over the reduced set of modulus parameters to identify values that minimize the desired objective function (step 820), as described in R. C. Chan et al., "OCT-based arterial elastography: robust estimation exploiting tissue biomechanics", Optics Express, Vol. 12(19), 2004, pp. 4558-4572, A. R. Skovoroda et al., "Tissue elasticity reconstruction based on ultrasonic displacement and strain images", IEEE Trans Ultrason Ferroelectr Freq Control, Vol. 42, 1995, pp. 747-765, and F. Kallel et al., "Tissue elasticity reconstruction using linear perturbation method", IEEE Trans Med Imaging, Vol. 15, 1996, pp. 299-313.

e. Determine objective function value at each element (step 825). Elements with objective function values exceeding a pre-determined tolerance threshold correspond to locations where the finite element model poorly fits the data. These elements can form a list for further refinement.

f. Sub-divide elements in the refinement list to form new, smaller elements spanning the space occupied by the original element (step 830). Each of these refined elements may have an independent modulus value initialized to the modulus estimated for the original element tissue class.

g. Repeat steps 820-825 using a constrained optimization scheme for the refined elements so that values vary over a limited range typical of the original tissue class assignment (step 835).

h. At convergence, display final strain and modulus distributions (step 840).

With appropriate tuning of the threshold for mesh refinement, the number of unknown parameters can be significantly reduced from the full dimensionality of the traditional approach in which all elements are treated as independent unknowns.

The foregoing merely illustrates the principles of the invention. Various modifications and alterations to the described embodiments will be apparent to those skilled in the art in view of the teachings herein. For example, the invention described herein is usable with the exemplary methods, systems and apparatus described in U.S. Provisional Patent Application No. 60/514,769 filed Oct. 27, 2003, and International Patent Application No. PCT/US03/02349 filed on Jan. 24, 2003, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced above are incorporated herein by reference in their entireties.

What is claimed is:

1. A system for determining data associated with at least one structural change of tissue, comprising:
   a non-transitory processing arrangement, which when executing a predetermined technique, is configured to:
     a) receive a first interferometric signal which contains first information regarding the tissue at a first stress level, and a second interferometric signal which contains second information regarding the tissue at a second stress level,
     b) compare the first and second information to produce comparison information, and
     c) determine the data associated with the at least one structural change as a function of the comparison information and further information associated with at least one of (i) at least one known characteristics of at least one of the tissue or an imaging agent within the tissue, or (ii) characteristics of an interferometric system, wherein the data includes an elastic modulus distribution in the tissue.

2. The system according to claim 1, wherein the at least one structural change is a strain of the tissue.

3. The system according to claim 1, wherein the second stress is different from the first stress.

4. The system according to claim 3, wherein the further information includes at least one of a velocity distribution of the tissue, a mechanical characteristic of the tissue, a tissue type, or a structure of the tissue.

5. The system according to claim 4, wherein the mechanical characteristic is at least one of a compressibility characteristic or an elasticity characteristic.

6. The system according to claim 4, wherein the processing arrangement is further configured to determine the velocity distribution of the tissue based on a Doppler signal obtained from the tissue.

7. The method apparatus according to claim 1, wherein the processing arrangement generates the elastic modulus distribution graphically as at least one image.

8. A method for determining data associated with at least one structural change of tissue, comprising the steps of:
   receiving a first interferometric signal which contains first information regarding the tissue at a first stress level, and a second interferometric signal which contains second information regarding the tissue at a second stress level;
   comparing the first and second information to produce comparison information; and
   using a processor, determining the data associated with the at least one structural change as a function of the comparison information and further information associated with at least one of (i) at least one known characteristics of at least one of the tissue or an imaging agent within the tissue, or (ii) characteristics of an interferometric system, wherein the data includes an elastic modulus distribution in the tissue.

9. The method according to claim 8, wherein the at least one structural change is a strain of the tissue.

10. The method according to claim 9, further comprising the step of determining the velocity distribution of the tissue based on a Doppler signal obtained from the tissue.

11. The method according to claim 8, wherein the second stress is different from the first stress.

12. The method according to claim 8, wherein the further information includes at least one of a velocity distribution of the tissue, at least one of a compressibility characteristic or an elasticity characteristic of the tissue, a tissue type, or a structure of the tissue.

13. A software arrangement for determining data associated with at least one structural change of tissue, comprising:
   a first set of instruction, provided on a non-transitory computer-accessible medium which, when executed by a tangible processing arrangement, configure the processing arrangement to receive a first interferometric signal which contains first information regarding the tissue at a first stress level, and a second interferometric signal which contains second information regarding the tissue at a second stress level;
   a second set of instruction, provided on the computer accessible medium, which the processing arrangement to when executed by a processing arrangement, configure the processing arrangement to compare the first and second information to produce comparison information; and
   a third set of instruction, provided on the computer-accessible medium, which when executed by the processing arrangement, configure the processing arrangement to determine the data associated with the at least one structural change as a function of the comparison information and further information associated with at least one of (i) at least one known characteristics of at least one of the tissue or an imaging agent within the tissue, or (ii) characteristics of an OCT system, wherein the data includes an elastic modulus distribution in the tissue.

14. The software arrangement according to claim 13, wherein the at least one structural change is a strain of the tissue.

15. The software arrangement according to claim 14, wherein the second stress is different from the first stress.

16. The software arrangement according to claim 13, wherein the further information includes at least one of a velocity distribution of the tissue, a compressibility characteristic of the tissue, a tissue type, or a structure of the tissue.

17. The software arrangement according to claim 16, further comprising a first set of instruction, which, when executed by a processing arrangement, configure the processing arrangement to determine the velocity distribution of the tissue based on a Doppler signal obtained from the tissue.

18. A system for determining data associated with at least one elastic modulus distribution of a tissue, comprising:
   a non-transitory processing arrangement, which when executing a predetermined technique, is configured to:
   a) receive at least one interferometric signal which contains information regarding the tissue, and
   b) determine the at least one elastic modulus distribution of the tissue as a function of the received at least one interferometric signal.

19. The system according to claim 18, wherein the information includes at least one of a structure of the tissue and a composition of the tissue.

20. The system according to claim 18, wherein the at least one interferometric signal includes a first interferometric signal which contains first information regarding the tissue at a first stress level, and a second interferometric signal which contains second information regarding the tissue at a second stress level, and wherein the second stress is different from the first stress.

21. The system according to claim 20, wherein the processing arrangement is further configured to compare the first and second information to produce comparison information, wherein the modulus is determined as a function of the comparison information.

22. The system according to claim 20, wherein the processing arrangement is further configured to generate a numerical model as a function of at least one of the first information or the second information.

23. The system according to claim 22, wherein the numerical model is a dynamic numerical model.

24. The system according to claim 23, wherein the dynamic numerical model includes at least one of constraints, a model complexity or a model order which are modifiable as a function of at least one of the first information or the second information.

25. The system according to claim 24, wherein the model complexity or a model order are modifiable as a function of at least one of the first information or the second information.

26. The system according to claim 24, wherein the dynamic numerical model is executed to produce further information, and wherein the further information is provided to the dynamic numerical model so as to modify the at least one of the constraints, the model complexity or the model order.

27. The system according to claim 24, wherein the model complexity includes a plurality of model elements, at least first one of the elements being associated with at least second one of the elements based on weights of the first and second ones of the elements.

28. The system according to claim 22, wherein the processing arrangement is further configured to generate further information regarding the tissue using the numerical model, and wherein the further information is associated with a response of the tissue to stress applied to the tissue.

29. The system according to claim 28, wherein the processing arrangement is further configured to generate further data as a function of the comparison information and the further information.

30. The system according to claim 29, wherein the processing arrangement is further configured to modify the numerical model as a function of the further data.

31. The system according to claim 30, wherein the modulus is determined based on the numerical model.

32. The system according to claim 30, wherein the processing arrangement is further configured to determine strain information of the tissue based on the numerical model.

33. The system according to claim 21, wherein the comparison information is additionally dependent on further information which is at least one of (i) at least one known characteristics of the at least one of the tissue or the imaging agent within the tissue and (ii) characteristics of an interferometric system.

34. The system according to claim 33, wherein the further information includes at least one of a velocity distribution of the tissue, at least one of a compressibility characteristic or an elasticity characteristic of the tissue, a tissue type, and a structure of the tissue.

35. The system according to claim 34, wherein the processing arrangement is further configured to determine the velocity distribution of the tissue based on a Doppler signal obtained from the tissue.

36. The system according to 18, wherein the information regarding the tissue includes a velocity distribution of the tissue.

37. The system according to claim 36, wherein the processing arrangement is further configured to determine the velocity distribution of the tissue as a function of a Doppler signal obtained from the tissue.

38. The system according to claim 18, wherein the modulus includes an elastic modulus.

39. A method for determining data associated with at least one elastic modulus distribution of a tissue, comprising the steps of:
   a) receiving at least one interferometric signal which contains information regarding the tissue; and
   b) using a processor, determining the at least one elastic modulus distribution of the tissue as a function of the received at least one interferometric signal.

40. The method according to claim 39, wherein the information includes at least one of a structure of the tissue and a composition of the tissue.

41. The method according to claim 39, wherein the at least one interferometric signal includes a first interferometric signal which contains first information regarding the tissue at a first stress level, and a second interferometric signal which contains second information regarding the tissue at a second stress level, and wherein the second stress is different from the first stress.

42. The method according to claim 41, further comprising the step of comparing the first and second information to produce comparison information, wherein the modulus is determined as a function of the comparison information.

43. The method according to claim 41, further comprising the step of generating a numerical model as a function of at least one of the first information and the second information.

44. The method according to claim 43, further comprising the step of generating further information regarding the tissue using the numerical model, and
   wherein the further information is associated with a response of the tissue to stress applied to the tissue.

45. The method according to claim 44, further comprising the step of generating further data as a function of the comparison information and the further information.

46. The method according to claim 45, further comprising the step of modifying the numerical model as a function of the further data.

47. The method according to claim 46, wherein the modulus is determined based on the numerical model.

48. The method according to claim 46, further comprising the step of determining strain information of the tissue based on the numerical model.

49. The method according to claim 42, wherein the comparison information is additionally dependent on further information which is at least one of (i) at least one known characteristics of the at least one of the tissue or the imaging agent within the tissue and (ii) characteristics of an OCT system.

50. The method according to claim 49, wherein the further information includes at least one of a velocity distribution of the tissue, at least one of a compressibility characteristic or an elasticity characteristic of the tissue type, and a structure of the tissue.

51. The method according to claim 50, further comprising the step of determining the velocity distribution of the tissue based on a Doppler signal obtained from the tissue.

52. The method according to claim 39, wherein the information regarding the tissue includes a velocity distribution of the tissue.

53. The system according to claim 52, further comprising determining the velocity distribution of the tissue as a function of a Doppler signal obtained from the tissue.

54. The method according to claim 39, wherein the modulus includes an elastic modulus.

55. A software arrangement for determining data associated with at least one elastic modulus distribution of a tissue, comprising:
   a first set of instruction provided on a non-transitory computer-accessible medium, which, when executed by a tangible processing arrangement, configure the processing arrangement to receive at least one interferometric signal which contains information regarding the tissue; and
   a second set of instruction provided on the computer-accessible medium, which, when executed by the processing arrangement, configure the processing arrangement to determine the at least one elastic modulus distribution of the tissue as a function of the received at least one interferometric signal.

56. The software arrangement according to claim 55, wherein the information regarding the tissue includes a velocity distribution of the tissue.

57. The software arrangement according to claim 56, further comprising a second set of instruction provided on the computer-accessible medium, which, when executed by the processing arrangement, configure the processing arrangement to determine the velocity distribution of the tissue as a function of a Doppler signal obtained from the tissue.

58. The software arrangement according to claim 55, wherein the modulus includes an elastic modulus.

* * * * *

UNITED STATES PATENT AND TRADEMARK OFFICE
CERTIFICATE OF CORRECTION

PATENT NO. : 8,965,487 B2
APPLICATION NO. : 11/211482
DATED : February 24, 2015
INVENTOR(S) : Brett Eugene Bouma, Raymond C. Chan and Guillermo J. Tearney It is certified that error appears in the above-identified patent and that said Letters Patent is hereby corrected as shown below:

In the Specification

Under column 1, after the "CROSS-REFERENCE TO RELATED APPLICATION(S)" section, please add the following paragraph as follows:

STATEMENT REGARDING FEDERALLY SPONSORED RESEARCH
This invention was made with Government support under Grant No(s). DAMD17-99-2-9001 awarded by the U.S. Army Medical Research and Material Command. The Government has certain rights in this invention.

Signed and Sealed this
Twenty-eighth Day of July, 2015

Michelle K. Lee
*Director of the United States Patent and Trademark Office*